United States Patent [19]
Kane et al.

[11] Patent Number: 6,063,251
[45] Date of Patent: May 16, 2000

[54] ELECTRICALLY INSULATED CAPILLARY ARRAYS FOR ELECTROPHORETIC APPLICATIONS

[75] Inventors: Thomas E. Kane, State College; John R. Kernan, Loganton; Changsheng Liu; Qingbo Li, both of State College, all of Pa.

[73] Assignee: Spectrumedix Corporation, State College, Pa.

[21] Appl. No.: 08/866,308

[22] Filed: May 30, 1997

[51] Int. Cl.[7] .................................................. G01N 27/447
[52] U.S. Cl. ........................ 204/601; 204/603; 204/604; 204/605
[58] Field of Search .................................. 204/451, 452, 204/454, 455, 601–605

[56] References Cited

U.S. PATENT DOCUMENTS

| | | |
|---|---|---|
| 5,085,757 | 2/1992 | Karger et al. . |
| 5,198,091 | 3/1993 | Burolla et al. . |
| 5,235,409 | 8/1993 | Burgi et al. . |
| 5,240,585 | 8/1993 | Young et al. . |
| 5,274,240 | 12/1993 | Mathies et al. . |
| 5,277,780 | 1/1994 | Kambara ................................. 204/604 |
| 5,332,480 | 7/1994 | Datta et al. . |
| 5,332,481 | 7/1994 | Guttman . |
| 5,356,525 | 10/1994 | Goodale et al. ..................... 204/299 R |
| 5,413,686 | 5/1995 | Klein et al. . |
| 5,417,923 | 5/1995 | Goodale et al. ......................... 422/103 |
| 5,436,130 | 7/1995 | Mathies et al. ............................. 435/6 |
| 5,498,324 | 3/1996 | Yeung et al. ............................ 204/452 |
| 5,605,666 | 2/1997 | Goodale et al. ......................... 422/103 |
| 5,635,050 | 6/1997 | Pentoney, Jr. et al. . |
| 5,730,850 | 3/1998 | Kambara et al. ........................ 204/603 |

FOREIGN PATENT DOCUMENTS

| | | |
|---|---|---|
| 0257855 | 3/1988 | European Pat. Off. . |
| 0723149 | 7/1996 | European Pat. Off. . |
| 9011484 | 10/1990 | Germany . |
| 2113903 | 8/1983 | United Kingdom . |
| 8904966 | 10/1990 | WIPO . |
| 9429712 | 12/1994 | WIPO . |
| 9429713 | 12/1994 | WIPO . |

OTHER PUBLICATIONS

International Search Report for PCT/US98/13667, dated Oct. 30, 1998.

*Primary Examiner*—William H. Beisner

[57] ABSTRACT

An automated electrophoretic system is disclosed. The system employs a capillary cartridge having a plurality of capillary tubes. The cartridge has a first array of capillary ends projecting from one side of a plate. The first array of capillary ends are spaced apart in substantially the same manner as the wells of a microtitre tray of standard size. This allows one to simultaneously perform capillary electrophoresis on samples present in each of the wells of the tray. Electrical crosstalk between neighboring capillaries is attenuated using a protective tubing formed from an electrically insulative material. This crosstalk attenuation is provided in the form of sheathing, either around individual capillaries, or around bundles of spaced apart capillaries. Crosstalk attenuation may be enhanced by passing a nonconductive gas or liquid through lumens formed in the protective tubing, in which lumens the capillary tubes are present.

16 Claims, 15 Drawing Sheets

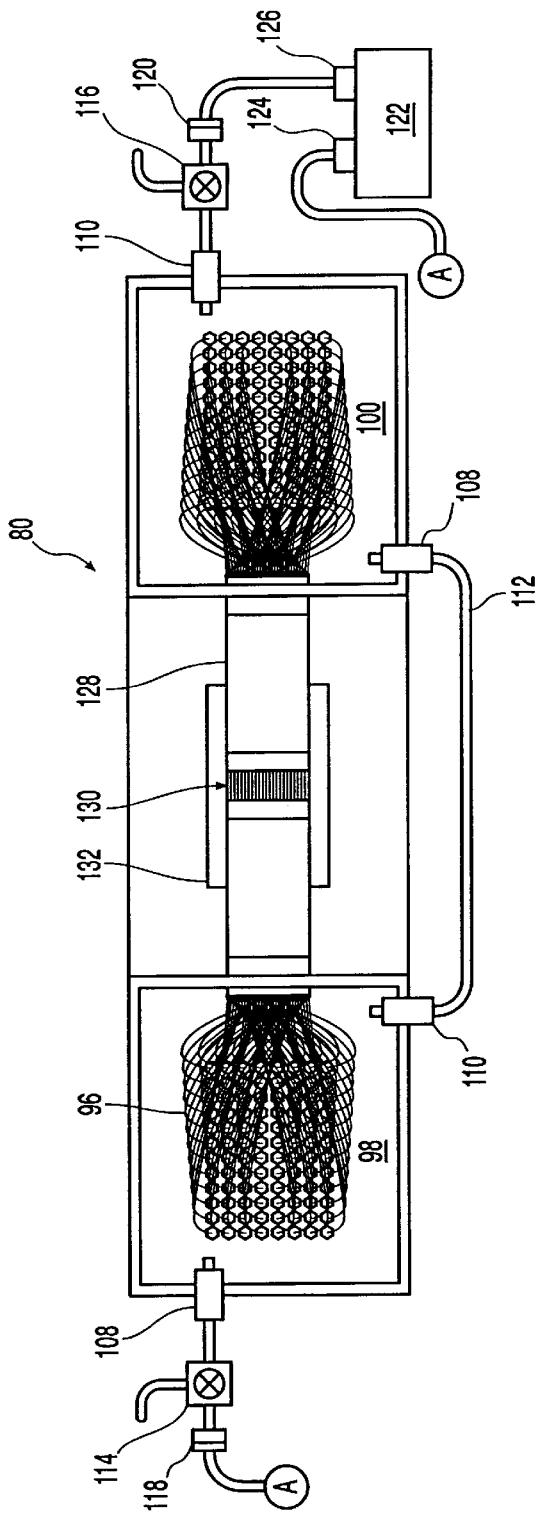
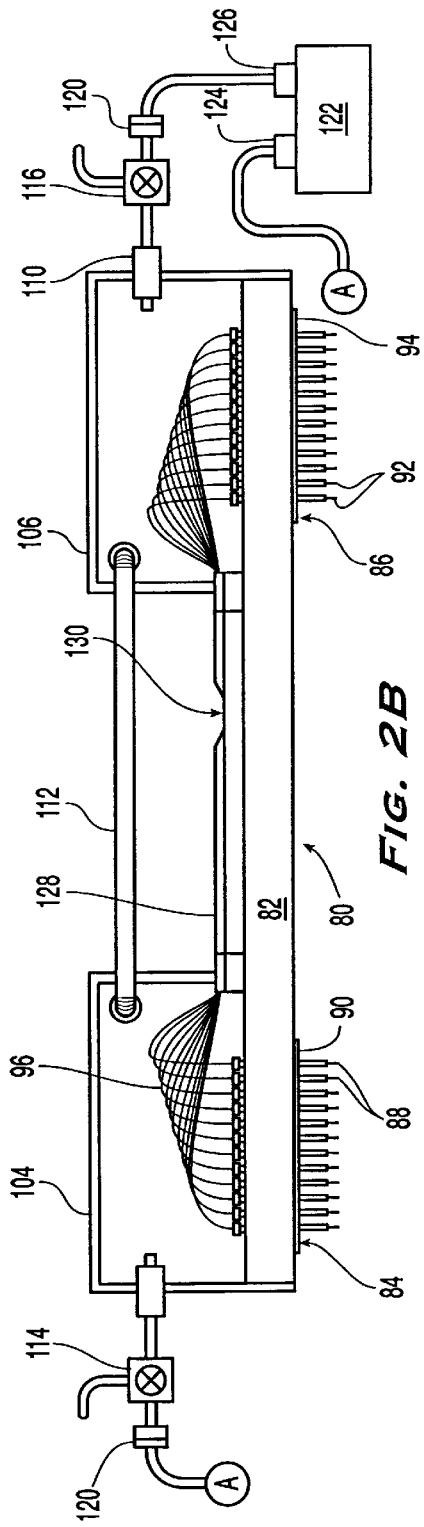
FIG. 2A
FIG. 2B

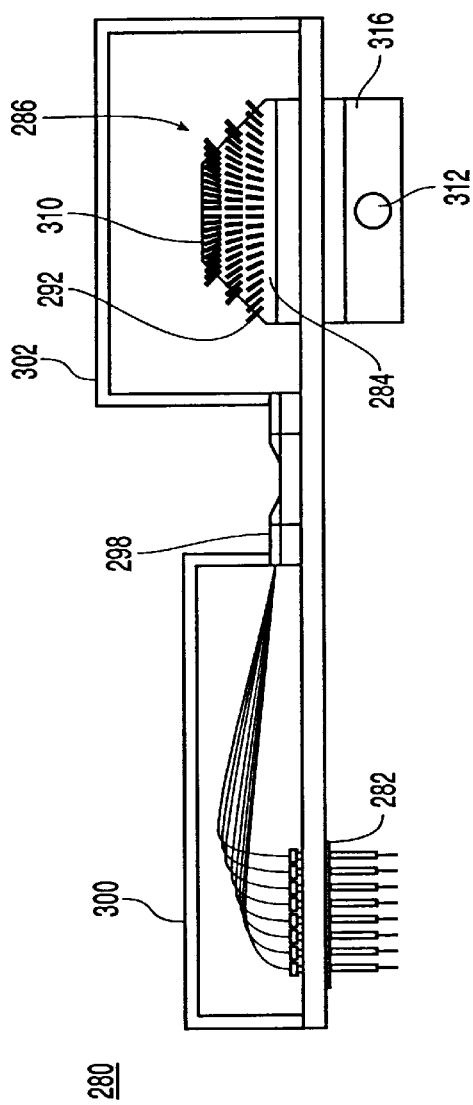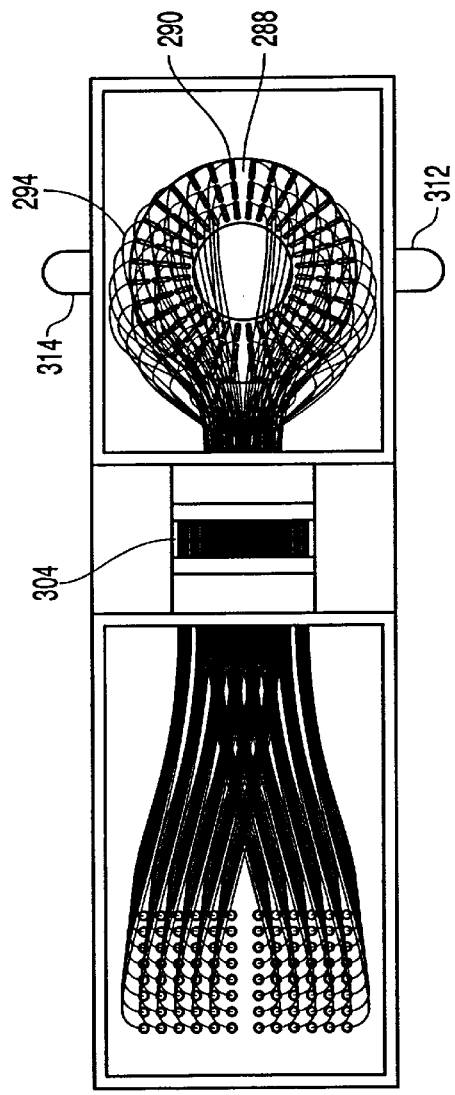

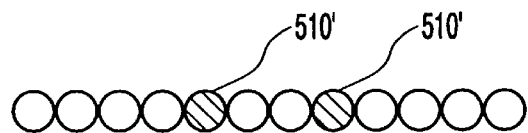
FIG. 12A
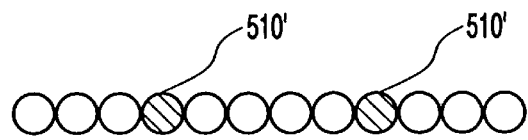
FIG. 12B
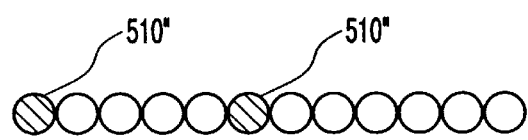
FIG. 12C
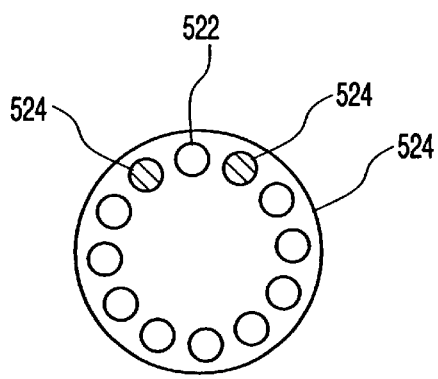
FIG. 14A
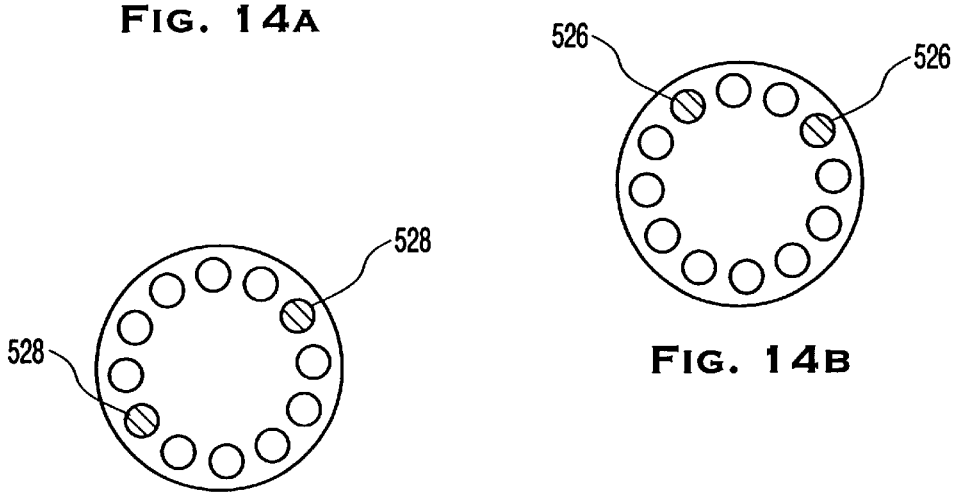
FIG. 14B
FIG. 14C

ELECTRICALLY INSULATED CAPILLARY ARRAYS FOR ELECTROPHORETIC APPLICATIONS

TECHNICAL FIELD

This invention relates to an apparatus for performing electrophoresis. More particularly, it pertains to an automated electrophoresis system employing capillary cartridges which are configured for use with commercially available, microtitre trays of standard size and are provided with sheathing to attenuate electrical crosstalk between neighboring capillaries during electrophoresis.

BACKGROUND

Electrophoresis is a well-known technique for separating macromolecules. In electrophoretic applications, molecules in a sample to be tested are migrated in a medium across which a voltage potential is applied. Oftentimes, the sample is propagated through a gel which acts as a sieving matrix to help retard and separate the individual molecules as they migrate.

One application of gel electrophoresis is in DNA sequencing. Prior to electrophoresis analysis, the DNA sample is prepared using well-known methods. The result is a solution of DNA fragments of all possible lengths corresponding to the same total sequential order, with each fragment terminated with a tag label corresponding to the identity of the given terminal base.

The separation process employs a capillary tube filled with conductive gel. To introduce the sample, one end of the tube is placed into the DNA reaction vial. After a small amount of sample enters the capillary end, both capillary ends are then placed in separate buffer solutions. A voltage potential is then applied across the capillary tube. The voltage drop causes the DNA sample to migrate from one end of the capillary to the other. Differences in the migration rates of the DNA fragments cause the sample to separate into bands of similar-length fragments. As the bands traverse the capillary tube, the bands are typically read at some point along the capillary tube using one of several detection techniques.

Usually, multiple DNA preparation reactions are performed in a commercially available microtitre tray having many separate low-volume wells, each holding on the order of 200–1000 micro-liters. The microtitre trays come in standard sizes. In the biotech industry, the currently preferred microtitre tray has a rectangular array comprising of 8 rows and 12 columns of wells. The centers of adjacent wells found in a single row are separated by approximately 0.9 cm, although this figure may vary by one or two tenths of a millimeter. The same holds for the spacing between adjacent wells in a single column. The rectangular array of 96 wells has a footprint within an area less than 7.5 cm×11 cm.

Miniaturization has allowed more wells to be accommodated in a single microtitre tray having the same footprint. New trays having four times the density of wells within the same footprint have already been introduced and are fast becoming the industry standard. Thus, these new trays have 16 rows and 24 columns with an inter-well spacing of approximately 0.45 cm.

It is not uncommon to analyze several thousand DNA samples for a given DNA sequencing project. Needless, to say, it is time consuming to employ a single capillary tube for several thousand runs.

Prior art devices have suggested means for analyzing DNA bands in multiple capillaries simultaneously. Such a device is disclosed in U.S. Pat. No. 5,498,324 to Yeung et al, whose contents are incorporated by reference in their entirety. This reference teaches a means for detecting the DNA bands as they are separated in multiple capillary tubes which are positioned parallel to another. However, in such an arrangement, each capillary tube is filled with gel and a sample is introduced into each capillary tube.

The arrangement described above takes a considerable amount of time to fill each capillary tube with gel. It also takes considerable effort to introduce a reaction sample into one end of each of the tubes reproducibly and reliably.

It is also not uncommon that one uses the same capillary tube for several consecutive sample runs. This, obviously risks cross-contamination of samples, which is a further disadvantage in certain prior art arrangements.

SUMMARY OF THE INVENTION

One object of the invention is to provide a device which allows one to simultaneously introduce samples into a plurality of capillary tubes directly from microtitre trays having a standard size.

Another object is to ensure that an apparatus for multiple-capillary electrophoresis can be provided with features to regulate capillary tube temperature.

Yet another object of the present invention is to mitigate the effects of electrical crosstalk between neighboring capillaries in such an apparatus.

These objects are achieved by a disposable capillary cartridge which can be cleaned between electrophoresis runs, the cartridge having a plurality of capillary tubes. A first end of each capillary tube is retained in a mounting plate, the first ends collectively forming an array in the mounting plate. The spacing between the first ends corresponds to the spacing between the centers of the wells of a microtitre tray having a standard size. Thus, the first ends of the capillary tubes can simultaneously be dipped into the samples present in the tray's wells. The cartridge is provided with a second mounting plate in which the second ends of the capillary tubes are retained.

Plate holes may be provided in each mounting plate and the capillary tubes inserted through these plate holes. In such case, the plate holes are sealed airtight so that the side of the mounting plate having the exposed capillary ends can be pressurized. Application of a positive pressure in the vicinity of the capillary openings in this mounting plate allows for the introduction of air and fluids during electrophoretic operations and also can be used to force out gel and other materials from the capillary tubes during reconditioning. The capillary tubes may be protected from damage using a needle comprising a cannula and/or plastic tubes, and the like when they are placed in these plate holes. When metallic cannula or the like are used, they can serve as electrical contacts for current flow during electrophoresis.

To mitigate the effects of electrical crosstalk, an apparatus in accordance with the present invention can be provided with an electrically insulative material which surrounds the capillary tubes along at least a portion of their extent before reaching a window region of the capillary tubes. The insulative material takes the form of a nonconductive protective tubing formed from a material having a dielectric constant greater than that of air. The capillary tubes are threaded through a protective tube having at least one lumen formed therethrough. When more than one lumen is provide in a single protective tube, they are spaced apart in such a manner that the crosstalk effects on all capillary tubes is approximately the same. This can be done, for instance, by arranging the lumens equally around a circle formed along a periphery of the protective tubing. Multiple such protective tubings may be provided to ensure that all capillary tubes are protected in such a manner.

The lumens can be made large enough to permit a coolant material, such as a gas or liquid, to bathe the capillary tubes along at least a portion of their extent. The coolant may be circulated past the capillary tubes by means of a pump or other motive source. As the coolant is pumped, its temperature may also be regulated to ensure uniform environmental control across all capillary tubes.

Proximate to the capillary ends which are dipped into solution, the capillary tubes can be protected with an enclosure which surrounds substantially the same portion of all the capillary tubes, all together.

BRIEF DESCRIPTION OF THE DRAWINGS

FIGS. 2A and 2B are a top and side view, respectively, of one embodiment of a cartridge of the present invention;

FIGS. 6A and 6B are a side and a top view, respectively, of a second embodiment of a cartridge of the present invention;

FIGS. 12a–c show crosstalk symmetries in capillary tubes arranged in a linear arrays;

FIGS. 14a–c show crosstalk symmetries of capillary tubes arranged in bundles in multi-lumen tubing;

DETAILED DESCRIPTION OF THE PREFERRED EMBODIMENT

Figure 1:
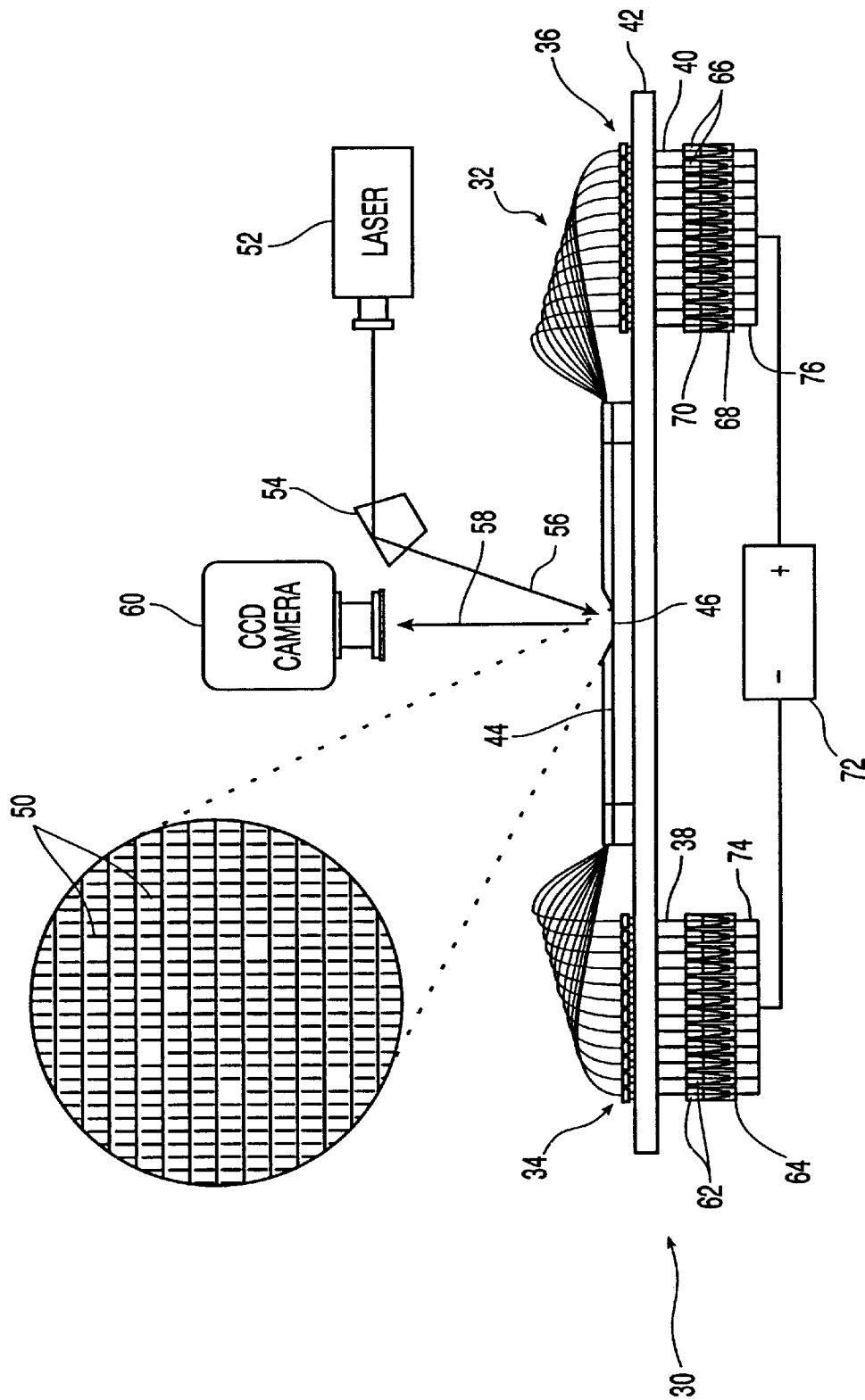
FIG. 1 is a side view of an arrangement in accordance with the present invention.

FIG. 1 presents a schematic illustrating the use of a device in accordance with the present invention. A cartridge 30 of the present invention comprises a plurality of capillary tubes 32 having substantially the same length. The capillary tubes extend between a sample-side connection array 34 and gel side connection array 36. The capillary tubes 32 terminate on the sample-side in an array of first capillary ends 38 and on the gel side in an array of second capillary ends 40.

Thus, both ends of each of the capillary tubes 32 in FIG. 1 extends through individual plate holes in a base member 42, which preferably is formed from polycarbonate, or acrylic or the like. Alternatively, each array of capillary ends may be retained in a separate mounting plate having the plate holes, and each of the mounting plates may then be fixed to a base member. Also, instead of passing each capillary tube through an individual plate hole, one or more capillary tubes may be collected together and sent through a common hole, or even no hole at all.

Between the two arrays, the capillary tubes 32 pass through a thermoelectric element 44 which is mounted on the base member 42. The thermoelectric element is arranged on either side of a window region 46. The thermoelectric element is used to control the temperature of the capillary tubes within a predetermined range. It should be evident to one skilled in the art that the thermoelectric element 42 may be comprised of two or more individual elements. It should also be evident that alternate temperature control means such as circulating fluid systems, and air convection may also be used to control the temperature.

The capillary tubes 32 are arranged parallel to one another, side by side, in the window region 46. The length of each capillary tube from its first capillary end to the window region 46 is substantially the same for all the capillary tubes 32. This length is determined by the optimization of (i.e., minimum acceptable) sample run time, and the minimum acceptable resolution of the separated samples. Nominally, this length in on the order of 50–70 cm. The window region 46 represents the region allowing access to the parallel capillary tubes from incoming excitation light. It also allows access to outgoing fluorescence emission from the capillary tubes. Thus, the window region 46 allows the bands 50 in the various capillary tubes to be detected.

As shown in FIG. 1, an excitation light source comprising a laser 52 and a prism 54 is used to focus a light beam 56 through the window region 46 and onto the capillary tubes 32.

A fluoresced light beam 58 is then sensed by a CCD camera 60, which captures the bands 50. As is known to those skilled in the art, other illumination and detection means can also be used.

The arrangement of FIG. 1 provides for the substantially simultaneous introduction of samples into the array of first capillary ends 38 of all the capillary tubes 32. In particular, the arrangement allows one to introduce the various samples by simultaneously dipping the array of first capillary ends 38 into the wells 62 of a sample-side microtitre tray 64 having a standard size, as described above.

To allow for this, the individual capillary ends are spaced apart from one another such that they have a spatial arrangement which is substantially the same as, that of an array of wells belonging to a microtitre tray of standard size. Thus, the spacing between adjacent first capillary ends is approximately 0.9 cm and the entire array of first capillary ends has a footprint less than 7.5 cm×11 cm, thus corresponding to a microtitre tray of standard size.

The array of second capillary ends 40 is inserted into the wells 66 of a second microtitre tray 68, where they come into contact with a buffer solution 70, as known to those skilled in the art. As the wells 66 in the second tray 68 are separated from one another, the chance of cross-contamination among the second capillary ends 40 is reduced.

A voltage source 72 is used to provide a voltage differential between the two arrays of capillary ends. As shown in FIG. 1, one voltage level is applied through individual leads 74 to each of the wells 62 of the first microtitre tray 64 and a second voltage level is applied in substantially the same manner through leads 76 to the wells 66 of the second tray 68. Thus, current flows through the leads 74, into the individual samples, through the first capillary ends 38, through the capillary tubes 32, through the second capillary ends 40, into the buffer 70 present in the wells 66 of the second microtitre tray 68, and finally through leads 76.

FIGS. 2A and 2B shows a top and a side view of one embodiment of a cartridge 80 in accordance with the present invention. The cartridge has a base member 82 formed from polycarbonate, acrylic or the like. Mounted in the base member are first and second mounting plates 84, 86, respectively. Preferably, these plates are formed from an electrically insulative material.

An array of first capillary ends 88 project from the bottom surface 90 of the first mounting plate 84 and an array of second capillary ends 92 project from the bottom surface 94 of the second mounting plate. The capillary tubes 96 pass through, and are retained in, plate holes formed in the plates 84, 86 and project from the top surfaces 98, 100 of the plates. Preferably, each of the capillary tubes 96 is protected by a tube assembly 102 which is secured to a plate hole in the mounting plate, as it passes through the mounting plates.

As best seen in FIG. 2A, the tube assemblies, each with its associated capillary tubes, form a rectangular array of 8 rows and 12 columns as they emerge from the plates 84, 86. The spacing between adjacent plate holes in which the assemblies 102 are held, and the spacing of adjacent capillary ends 88, 92 correspond to the spacing of adjacent wells in a microtitre tray of standard size. In the preferred embodiment, adjacent capillary ends are separated by approximately 0.9 cm and the entire array of capillary ends, and thus the array of plate holes through which the capillary tubes 96 pass, form a footprint no larger than about 7.5 cm×11.0 cm.

The upper surface 98, 100 of each mounting plate 84, 86 is provided with first and second enclosures designated by reference numerals 104, 106, respectively. In the preferred embodiment, each of the enclosures is provided with an inlet 108 and an outlet 110. The outlet 110 of the first enclosure is connected to the inlet 108 of the second enclosure by plastic tubing 112. The inlet 108 of the first enclosure is connected to a first plastic shut off valve 114 while the outlet 110 of the second enclosure is connected to a second plastic shut off valve 116. The plastic shut off valves 114, 116 are connected, in turn, to respective first and second quick disconnects 118, 120.

During operation, the cartridge 80 can be connected to a pump assembly 122 which is arranged to circulate a temperature-controlled liquid coolant through the enclosures 104, 106. In such case, the cartridge's first disconnect 118 is connected to the output 124 of the pump assembly 122 while the second disconnect 120 is connected to the input 126 of the pump assembly 122. Such an arrangement maintains the temperature of those portions of the capillary tubes 96 projecting from the upper surfaces 98, 100 of the mounting plates and present in the enclosures 104, 106. For this to work, the mounting plates 84, 86 must form a liquid-tight seal with the base member 82. A liquid-tight seal must also be formed between the plate holes and the tube assemblies 102 and/or the capillary tubes 96 themselves.

The capillary tubes 96 pass between the two arrays of tube assemblies 102 in an area of the cartridge not covered by the enclosures 104, 106. As explained above, thermoelectric temperature control means 128, or the equivalent, is arranged on either side of a window region 130 of the capillary tubes 96 to control the temperature of the capillary tubes when they are no longer within the enclosures 104, 106. Within at least a portion of the window region 130, the capillaries 96 are arranged parallel to one another so that they may be read by detection means. Preferably, the base member 82 is provided with an opening 132 above which the window region 130 is situated. This allows for at least one of illumination means or detection means to be placed below the base member from where they may be in a direct line of sight to the exposed capillary tubes 96.

Figure 3A:
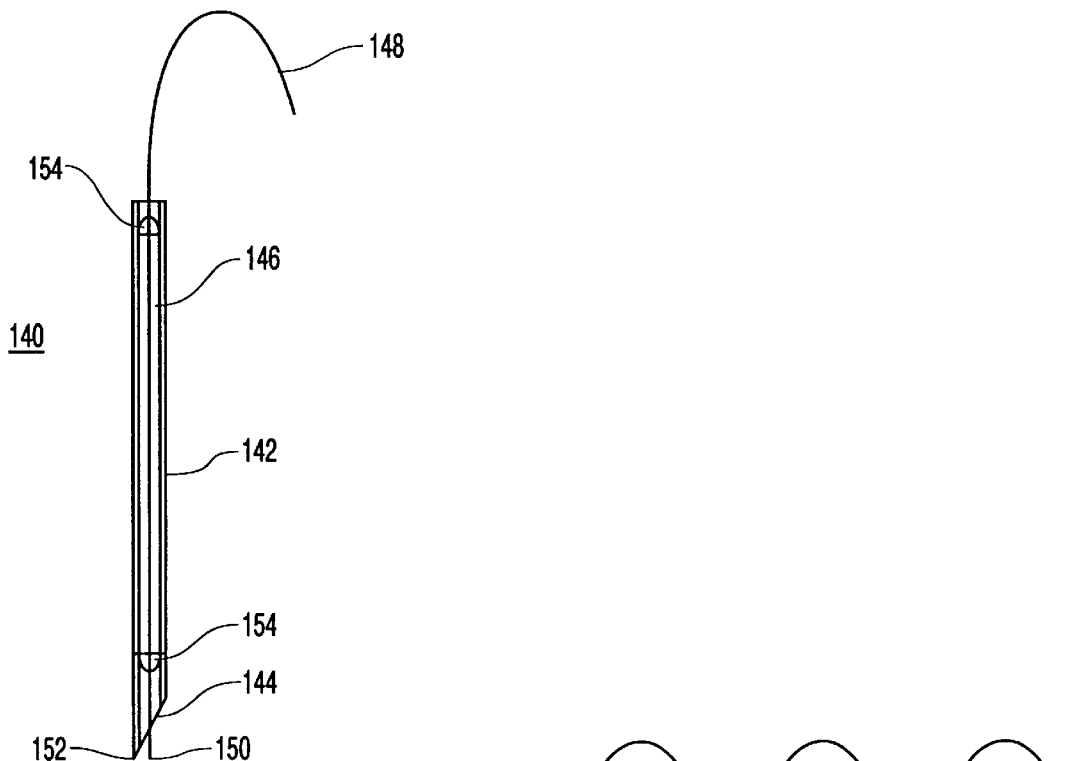
FIGS. 3A and 3B show a tube assembly and mounting arrangement for a cartridge of the present invention.
Figure 3B:
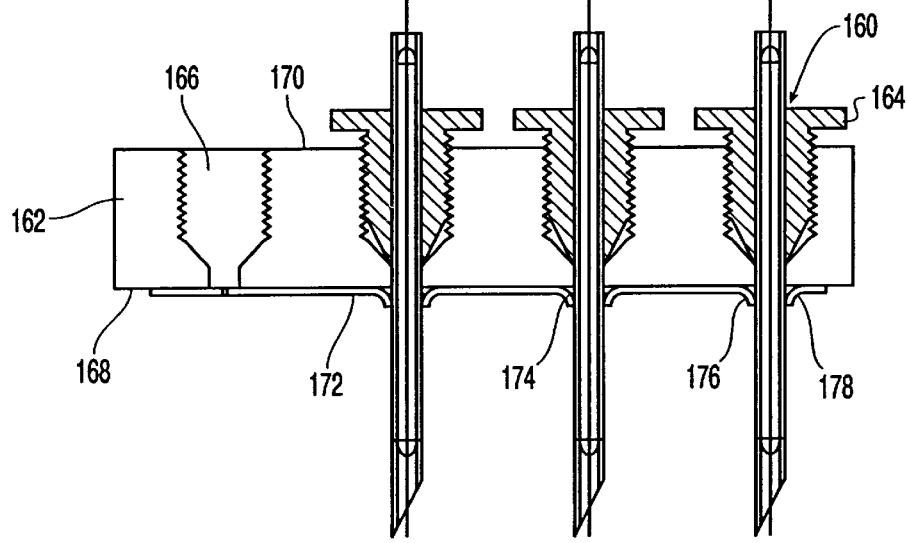

FIG. 3A shows a needle 140 used in forming a tube assembly 160 which can then be directly inserted into a mounting plate 162, as shown in FIG. 3B. The needle 140 comprises a metallic cannula 142. In the preferred embodiment, the cannula 142 is formed from stainless steel having an inner diameter of 0.064 in. and an outer diameter of 0.072 in. The cannula 142 is provided with a bevel 144 at the end which is dipped into a well.

Within the cannula 142 is a coaxially arranged annular polyetheretherketone (PEEK) polymer tubing 146 which serves as a sleeve. The polymer tubing 146 has an inner diameter of about 0.006 in. and an outer diameter of 0.0625 in. Thus, the polymer tubing 146 can be comfortably inserted into cannula 142.

Running through the center of the tubing 146, along a longitudinal axis of the needle 140, is a capillary tube 148 which is associated with the needle 140. The capillary tube 148 is formed from fused silica and has an inner diameter of about 0.003 in. and an outer diameter of about 0.006 in.

Thus, the capillary tube 148 fits snugly into the polymer tubing 146. The capillary tube 148 terminates in an end 150 which is substantially across from the end 152 of the cannula 142. Thus, the spacing between the two ends 150, 152 is about 0.035 in.

An UV-cured, medical-grade epoxy sealant 154 is used at both ends of the polymer tubing 146 to secure it and the capillary tube 148 to the cannula 142. Preferably, the epoxy sealant 154 forms an air- and liquid-tight seal through the cannula 142. The epoxy sealant ensures that the polymer tubing 146 is not exposed to the environment, and also ensures that the capillary tube 148 does not come into direct contact with the cannula 142.

It should be noted that a needle may be formed in ways other than the one depicted in FIG. 3A. For instance, instead of a tubular cannula, the needle may simply comprise a capillary tube encased in a poured or coextruded plastic material which, in turn, is secured to a metallic strip. Other arrangements are also possible.

FIG. 3B shows a hollow, high pressure compression fitting 164 formed from nylon into which the needle 140 is inserted to complete the tube assembly 160. The needle 140 can be secured to the cylindrical inner walls of the compression fitting with an epoxy sealant. Each tube assembly 160 is then inserted into a plate hole 166 tapped in the mounting plate 162 and the plate hole 116, too, can be sealed with epoxy. When this is done, an air- and liquid-tight seal is provided between the bottom surface 168 and the top surface 170 of the mounting plate 162, allowing the mounting plate to withstand a positive pressure applied on its bottom surface in a region where the plate holes securing the tube assemblies are situated.

One may completely do away with the compression fittings 164 and drill plate holes in the mounting plate 162 which correspond in size to the outer diameter of the needles 140. In such case, a needle is directly inserted into each plate hole in the mounting plate 140 and secured thereto by the epoxy. Such a fitting-less approach can improve the structural integrity of the mounting plate 162 due to the reduced size of the plate holes. It may also provide a better air- and liquid-tight seal since there are fewer interfaces in which epoxy sealant is used. Moreover, it should also be understood that one may retain just a capillary tube 148, or just a capillary tube 148 encased in polymer tubing 146 directly in a plate hole of appropriate size formed in the mounting plate 162.

Whether or not one uses a compression fitting, and whether or not one uses a cannula and/or polymer tubing, it should be understood that in the preferred embodiment, each plate hole has one capillary tube retained therein. The array of plate holes preferably has a spatial arrangement corresponding to that of the wells of a microtitre tray of standard size. However, it may be possible to form the plate holes off-center, and then angle the capillary ends.

Furthermore, it should also be understood that it may be possible to fix an array of capillary ends in the desired configuration without forming holes in a mounting plate 162. For instance, this can be done by gluing or clamping the individual capillaries to a mounting plate so that their ends are arranged in the desired configuration. Alternatively, the capillaries may be secured together so that their ends remain in the desired configuration in a poured acrylic or the like. What is important is that the spacing of the capillary ends in the array correspond to the spacing of the wells in the microtitre tray of standard size.

A conductive plate 172 may be secured to the mounting plate 162 by screws, adhesives, or other conventional means. The conductive plate 172 is formed with an array of conductive holes 174 which corresponds to the plate holes 166 in the mounting plate. Each of the conductive holes 174 is formed by an H-shaped slit which forms a pair of tabs 176, 178 between the legs of the "H". When a needle 140 is inserted in the conductive hole 174, the tabs 176, 178 give way, and contact either side of the needle 140.

As the entire plate 172 is conductive, all needles 140 in the array share a common electrical connection. A voltage applied to the conductive plate 172 then appears on the exterior of each needle 140 in the array. During electrophoretic application, this voltage appears in the buffer solution found in each well, into which solution the capillary end 150 is inserted.

As is known to those skilled in the art, the voltage differential may be delivered to the first capillary ends through other means as well. For instance, instead of contacting a common plate to which the needles are connected, voltage leads may be connected directly to each needle. Alternatively, individual leads may be dipped into the liquid in each well. Another alternative is to deliver the voltage through a metallic coating, such as gold, deposited on the exterior of only the terminal portion of each capillary tube, where it contacts the liquid in the well. Also, the voltage may be delivered directly to the wells through one or more leads, as described earlier. One skilled in the art can readily formulate alternative approaches to delivering a voltage to the first capillary end.

Figure 4:
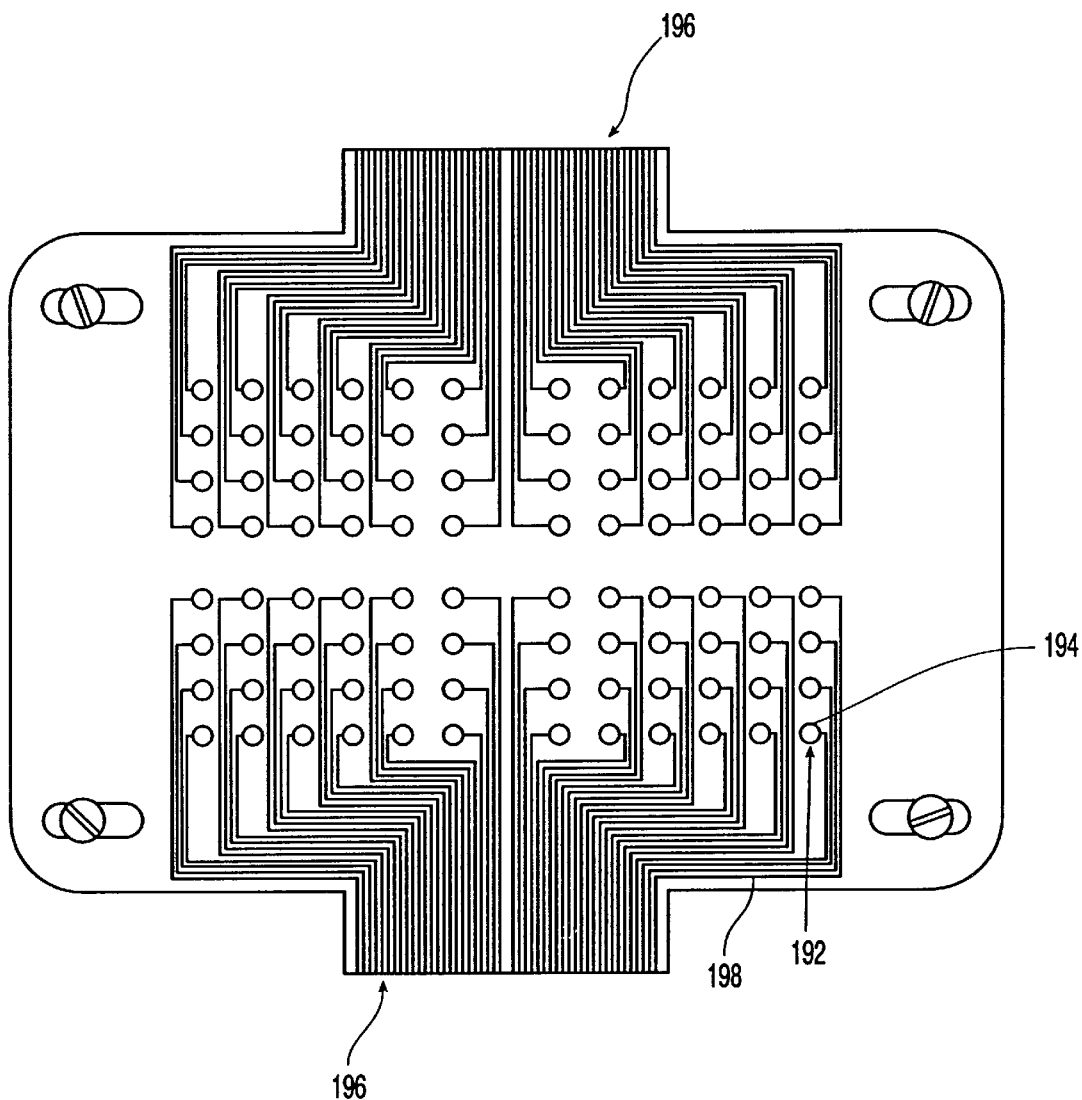
FIG. 4 shows a monitor plate which can be used with an array of needles.

FIG. 4 shows a monitor plate 190 which can be used with the cartridge embodiment shown in FIGS. 2A and 2B. In a cartridge of the present invention, the needles of at least the first mounting plate 84 are provided with a conductive plate 172 described above. The needles of the second mounting plate 86 can be provided with a monitor plate 190.

The monitor plate has an array of monitor holes 192. The array of monitor holes is aligned with the second array of plate holes formed in the second mounting plate 86. Each monitor hole 192 is formed with an isolated electrical contact 194 which is electrically connected to a monitor plate connector 196 by an individual lead 198. Each needle in the second mounting plate 86 contacts a corresponding electrical contact 194 in the monitor plate.

The purpose of the monitor plate is to provide a means for gauging the presence of electrical conductivity between any needle in the second mounting plate 86 and the needles of the first mounting plate 84. In this regard, it should be understood that the monitor plate 190 can be secured to mounting plate 86 in much the same manner as the conductive plate 172. What is important is that each of the electrical contacts 194 connects to only one needle in the second mounting plate.

Figure 5:
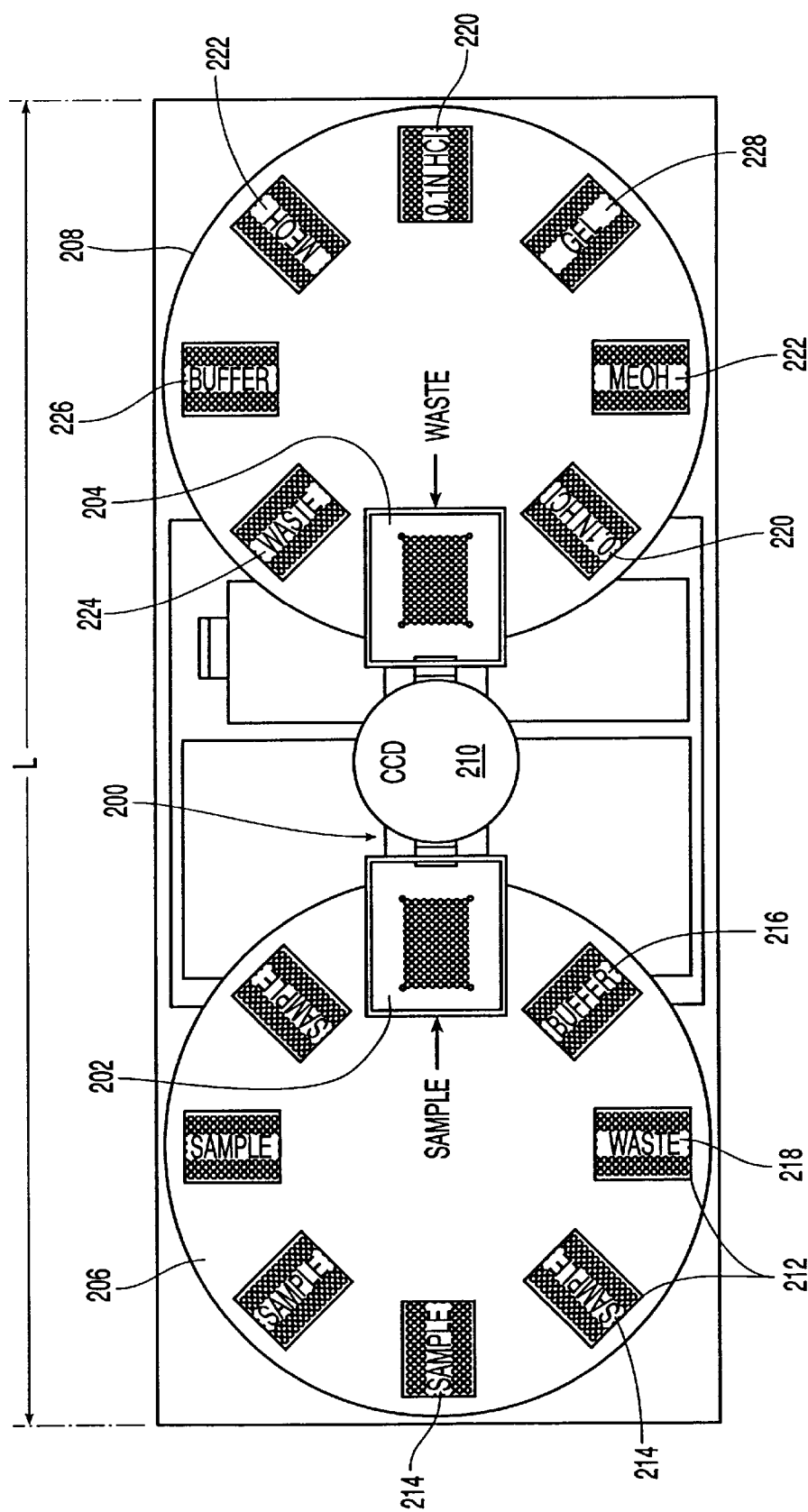
FIG. 5 shows the arrangement of an apparatus which can be used with the cartridge of FIGS. 2A & 2B.

FIG. 5 shows a cartridge 200 having a first 202 and a second 204 array of needles arranged above a first 206 and a second 208 carousel, each array positioned above a portion of a respective carousel. A CCD camera 210 is positioned above a portion of the cartridge between the two to detect bands in the capillary tubes (not shown in FIG. 5). Each carousel 206, 208, has eight platforms 212, on each of which a microtitre tray having a standard size is placed.

The wells in each of these trays hold one or more liquids such as samples, gels, buffer solutions, acidic solutions, basic solutions, etc. As configured in FIG. 5, the first carousel holds 6 sample trays 214, 1 buffer tray and 1 waste tray, a sample tray being positioned underneath the first needle array 202. As also shown in FIG. 5, the second carousel holds a pair of acidic solution trays 220, a pair of basic solution trays 222, a pair of waste trays 224, one of which is positioned underneath the second needle array 204, a buffer solution tray 226, and a gel tray 228. Thus, the first carousel 206 is the sample-side carousel and the second carousel 208 is the gel-side carousel.

The cartridge is removably mounted to an automated electrophoretic apparatus. During operation, a lifting means raises and lowers the platform 212 which is under either of the two needle arrays 202, 204. When a microtitre tray is brought in close proximity to one of the needle arrays 202, 204, the needles in these arrays, and their associated capillary ends, are dipped into the contents of each well of that microtitre tray. When the platform under either of the needle arrays is lowered, the carousel associated with that platform may be rotated so that a different platform 212 holding a different microtitre tray, can be raised.

When a platform is raised, surfaces around the periphery of the platform abut opposing surfaces, thus sealing a pressure chamber beneath the bottom surface of the needle array. Introducing a pressurized inert gas, such as helium, into the chamber at a pressure of 30 psi or so, applies a uniform force to the samples in the wells of the microtitre tray held on that platform. This causes a portion of each of samples to enter into the corresponding array of first capillary ends.

With, or in place of, applying pressurized helium to introduce samples into the first capillary ends, one may also apply a high voltage for brief period of time, on the order of 20–40 seconds, to cause the samples to migrate into the first capillary ends. Using a high voltage for this purpose, however, may be size-selective. That is, smaller molecules are more likely to enter the first capillary ends, potentially distorting the subsequent electrophoresis analysis.

The operation of the automated electrophoretic apparatus in accordance with FIG. 5 will now be described. First, the various microtitre trays are loaded with the designated buffer solutions, gels, samples, etc. Then, gel tray 228 in carousel 208 is raised and gel is introduced into the capillary tubes (not shown in FIG. 5) through second capillary ends (hidden in FIG. 5) associated with the second needle array 204. The gel tray 228 is then lowered. A sample tray 214 in carousel 206 is then raised, and sample is introduced through the first capillary ends (hidden in FIG. 5) associated with the first needle array 202. The sample tray 214 is then lowered. Carousels 206 and 208 are then rotated to position buffer trays 216 and 226 under their respective needle arrays 202 and 204. A voltage differential is then applied across the two needle arrays to perform the electrophoresis run.

Upon completion of the run, the cartridge may be reconditioned. This is done by flushing out the gel and samples from the previous run under pressure and cleaning the capillary tubes using the acidic 220 and/or basic 222 solutions. The cartridge is then ready for re-use, allowing the samples in another one of the sample trays 214 to be tested.

It should be obvious that the carousels 204, 206 may be formed with a different number of platforms. It should also be obvious that one can use a linear, or rectangular, or other arrangement of such platforms. All that is required is a storage and positioning system which allows a first particular microtitre tray to be brought to the first needle array 206, and a second particular microtitre tray to be brought under the second needle array 208.

FIGS. 6A and 6B present a side and a top view, respectively, of a cartridge 280 having a first mounting plate 282 in which the array of plate holes in the first mounting plate 282 is rotated by 90°. Otherwise, the arrangement for connecting the capillary tubes to the first mounting plate is substantially the same as previously described. The first capillary ends formed in an array with the desired spacing project from the bottom surface of the first mounting plate 282, and are retained in plate holes formed in the first mounting plate.

The second mounting plate 284, however, is not the same as in the previous cartridge embodiment. In the cartridge 280, the second mounting plate 282 serves as a pressure containment member of a pressure cell 286 having substantially cylindrical exterior walls. For the sake of clarity, FIG. 6A does not show all the capillary tubes on the first mounting plate, nor any capillary tubes at all on the second mounting plate 284. It is to be understood, however, that all the capillary tubes are present.

The second mounting plate has a radially symmetric, beveled surface 288 in which a plurality of plate holes 290 are formed. Each of these plate holes 290 is fitted with a section of PEEK polymer tubing 292 in which the capillaries are encased using an UV-cured epoxy, as described before, to form an air- and liquid-tight seal in the plate holes 290. The capillary tubes pass through the PEEK polymer tubing and a second end of each capillary tube communicates with an interior cavity of the pressure cell. Although the preferred embodiment for this cartridge uses just PEEK polymer tubing and a capillary tube in the second mounting plate, it should be understood, that needles similar to the ones described earlier, could also be used. Also, just the capillary tubes alone, secured by epoxy, can be used as well. What is important is that each capillary tube 294 is retained in a plate hole 290 in an air- and liquid-tight manner, and that the capillary tube's second end communicates with an interior cavity of the pressure cell 286.

As is the case with cartridge 80 of FIGS. 2A and 2B, this cartridge 280 is provided with thermoelectric control means 298, enclosures 300, 302, and its capillary tubes are arranged in parallel along at least a portion of a window region 304. Although not shown in FIGS. 6A and 6B, it is understood that the enclosures 300, 302 can be provided with inlets and outlets and the like for circulating a coolant, as was the case with the other cartridge 80.

As shown in FIG. 6A, the second mounting plate 284 has a truncated cone-shaped upper portion terminating in a flat top 310. The curved, conical surface 288 in which the plate holes 290 are formed, is advantageous for reasons of structural integrity when a high positive pressure is applied from underneath the second mounting plate. Also, placing the plate holes 290 on such a surface allows them to be placed farther apart, a feature which also enhances the structural integrity of the pressure cell 286.

The pressure cell 286 is secured to the base member of the cartridge 280 and projects through the bottom of the base member. This arrangement allows the pressure cell 286 to be provided with an inlet 312 and an outlet 314 arranged on opposite sides of its cylindrical exterior walls. It should be noted that the inlet could just as easily be formed in the flat top portion 310 of the second plate 284, and the outlet formed in the bottom surface of a lower portion 316 of the pressure cell 286. In such case, the pressure cell could be rest on the base member, rather than project through its bottom, with a pipe fitting connected to the outlet through a hole formed in the base member, which hole is then sealed.

Figure 7:
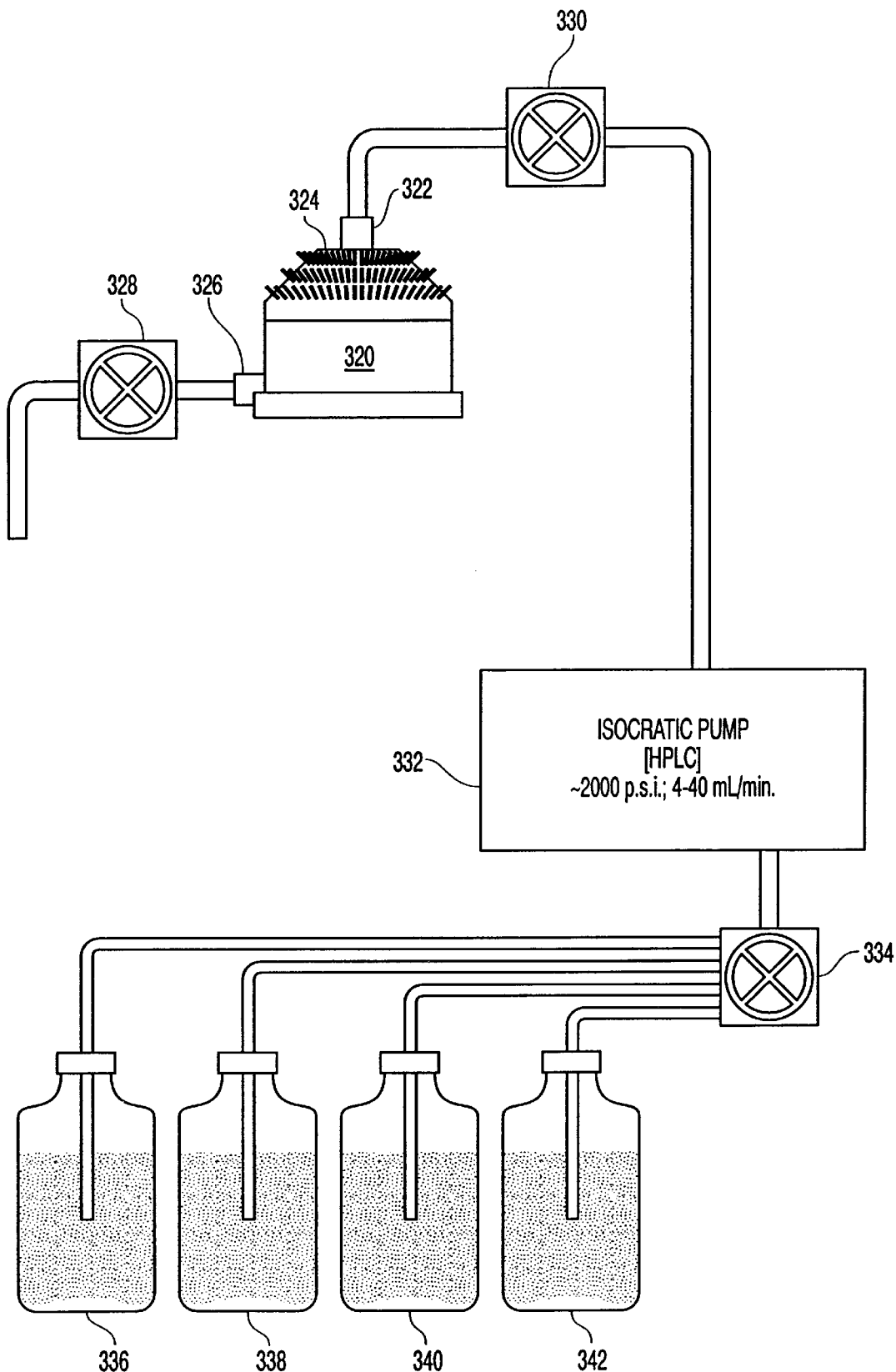
FIG. 7 shows the valving arrangement for a pressure cell similar to the one shown in the cartridge of FIGS. 6A and 6B.

FIG. 7 shows a valving arrangement for a pressure cell 320 which has an inlet 322 at its top surface 324, but otherwise is substantially similar to the pressure cell 286. Aside from the inlet 322, the pressure cell 320 is also provided with an outlet 326, which is connected to a waste valve 328. The waste valve 328 is opened to expel the contents of an interior cavity of the pressure cell 320.

Access to the inlet is 322 controlled by a shut-off valve 330. Liquids can be passed through the inlet 322 into the pressure cell 320 with the use of a pump 332. Preferably, the pump is a high pressure liquid chromatography (HPLC) pump having a pumping capacity of 4–40 milliliters per minute, at a pressure of about 2000 psi. The pump 332 is connected to a multi-valve manifold 334 which selectively allows one of four liquids to be pumped into the pressure cell. The four liquids are held in separate containers 336, 338, 340, 342, which respectively hold gel, a buffer solution, an acidic solution, and a basic solution. Additional containers holding the same liquids may be held in reserve, or connected in series with these, so as to increase the total supply.

The waste valve 328, the shut-off valve 330, the pump 332 and the multi-valve manifold 334 are all under the direction of a controller, preferably a microcomputer, or equivalent. Thus, the contents of an interior cavity of the pressure cell are regulated by the controller. Such a controller may also receive inputs from various pressure and temperature monitors and other sensors to prevent damage to the pressure cell 320.

During operation, the interior cavity of the pressure cell 320 is filled by means of the pump 332. This forces the pumped liquid into the second capillary ends which communicate with the interior cavity of the pressure cell 320. By filling the array of first capillary ends and the pressure cell 320 with the appropriate fluids in the appropriate sequence, one may perform the electrophoresis operations, much as described above with regard to the apparatus of FIG. 5.

After the run, one may recondition the pressure cell and the capillary tubes to prepare them for another run. Again, this is accomplished by flushing the gel and sample from all the capillary tubes simultaneously. With the pressure cell 320, however, pressures on the order of several thousand psi can be applied. These increased pressures force the viscous gel out of the capillary tubes much faster. This reduces the cycle time between runs, with reconditioning, to about one to two hours.

Figure 8:
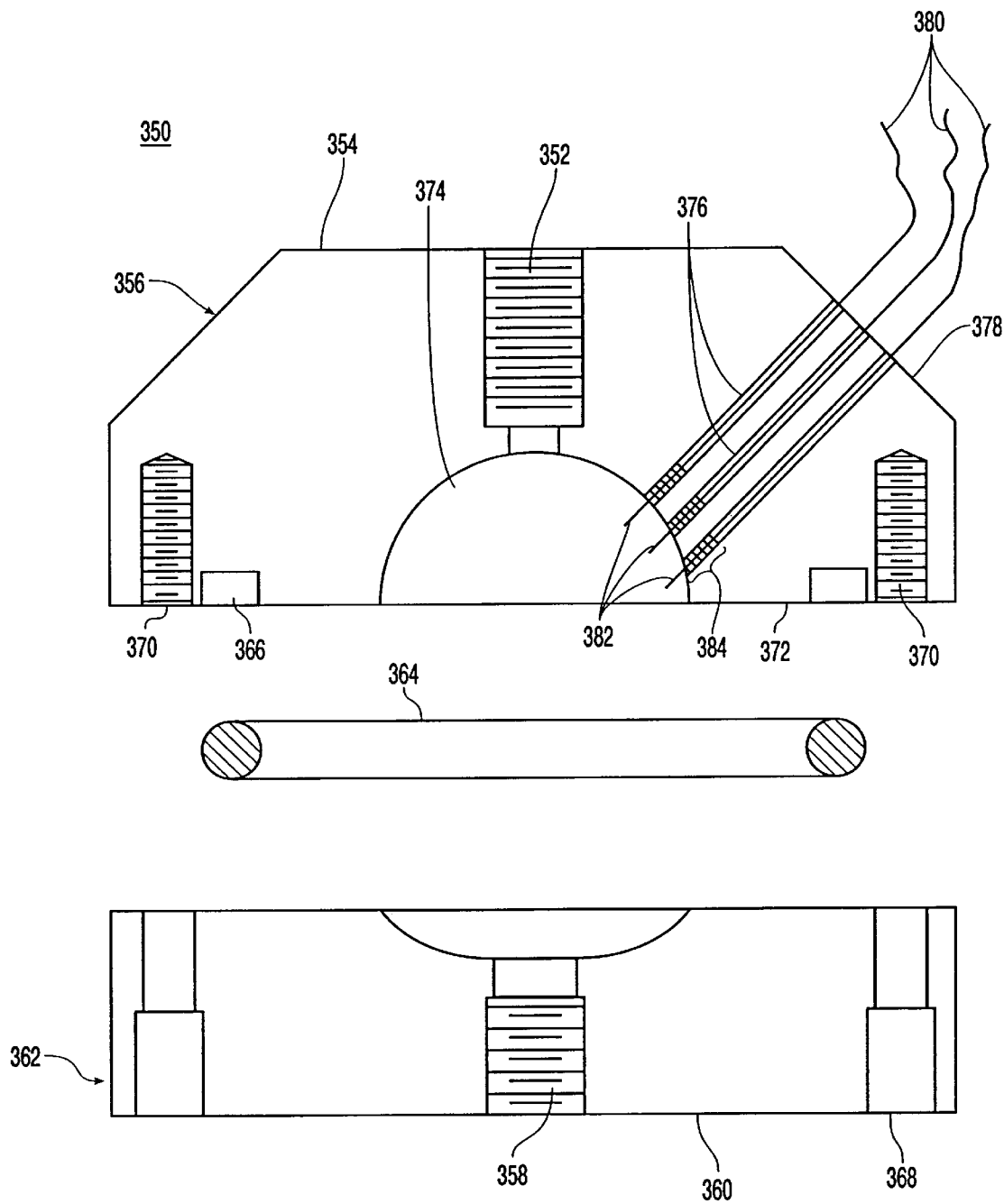
FIG. 8 shows an exploded view of a pressure cell vertical cross-section.

FIG. 8 shows an exploded cross-section of a pressure cell 350, similar to the pressure cell 286 in the cartridge 280. As is the case with the other pressure cells, pressure cell 350 is preferably formed from aluminum or stainless steel. The pressure cell 350 is provided with a threaded inlet 352 formed on the top surface 354 of its upper portion 356, which upper portion comprises the second mounting plate. The pressure cell 350 is also provided with a threaded outlet 358 on the bottom surface 360 of its lower portion 362. High pressure pipe fittings can be screwed into the threads of the inlet 352 and the outlet 358.

The upper portion 356 and the lower portion 362 are held together by a plurality of bolts (not shown) which are inserted through bolt holes 368 formed along the periphery of the bottom surface 360 of the lower portion 362. The bolts are then screwed into corresponding threaded holes 370 formed on the bottom surface 372 of the upper portion 356. An O-ring 364 partially fits into a rectangular channel 366 formed in the second mounting plate 356. The O-ring 364 provides a seal between the upper portion 356 and the lower portion 362. Instead of an O-ring, a gasket, or the like may be used to effect such a seal.

At the center of the pressure cell 350, formed between the upper 356 and lower 362 portions is an interior cavity 374. A plurality of plate holes 376 are formed in the upper portion (second mounting plate). For simplicity, in FIG. 8, the plate holes 376 are only shown on one side of the upper portion 356. It should be understood, however, that they are also present on the other side. The plate holes 376 extend from a beveled surface 378 formed on the upper portion 356 to the interior cavity 374.

Capillary tubes 380 are retained in these plate holes 376 and their second ends 382 communicate with the interior cavity 374. Preferably, each capillary is encased in a section of PEEK polymer tubing which extends from a point within each plate hole 376, proximate to the interior cavity 374, to well outside the beveled surface 378. For simplicity, however, the PEEK tubing is not shown in FIG. 8. Nevertheless, it should be kept in mind that just the capillary tube, or a needle comprising a capillary tube, PEEK tubing and a cannula, can be inserted into each plate hole 376, assuming that it is suitably sized.

As explained above, an UV-cured epoxy sealant is used to seal the plate holes 376 at both ends so that they are air- and liquid-tight. With the pressure cell, the terminal portion 384 of each plate hole proximate to the interior cavity 374 is tapped or roughened. This provides a surface to which the epoxy sealant bonds more readily during assembly.

A liquid held within the interior cavity 374 is in contact with the material forming the interior cavity. When the liquid is also in contact with the second capillary end 382, an electrical connection between the interior cavity 374 of the pressure cell 350 and the first capillary end secured to the first mounting plate, is completed. Thus, grounding the pressure cell 350 through a contact formed thereon, applies the ground to the interior cavity 374, completing the circuit necessary to perform the electrophoresis. Alternatively, as the pressure cell 350 is electrically isolated from the base member to which it is mounted, the potential of the pressure cell 350 may be allowed to float. This allows one to apply a high voltage to the pressure cell 350, rather than to the needles associated with the first capillary ends.

Figure 9:
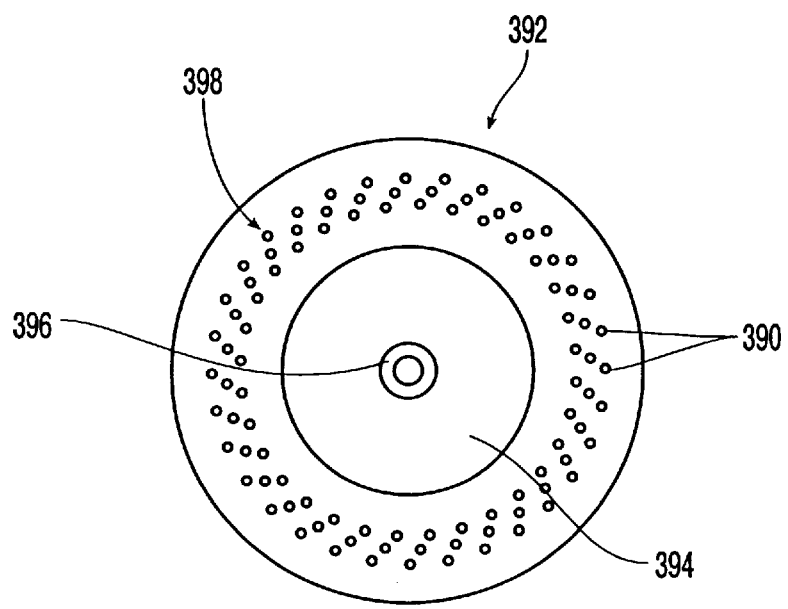
FIG. 9 shows a top view of a second mounting plate of a pressure cell having an alternate arrangement of plate holes.

FIG. 9 shows an alternate arrangement for the plate holes 390 in a second mounting plate 392 having a top surface 394 and an inlet 396. In this arrangement, each set 398 of three plate holes is offset at an angle relative to the center of the top surface 394. This provides for a maximum spacing between the plate holes. From a structural integrity point of view, such an arrangement may be preferable to having the plate holes arranged radially, in a spoke-like fashion, as shown in FIG. 6B.

Figure 10:
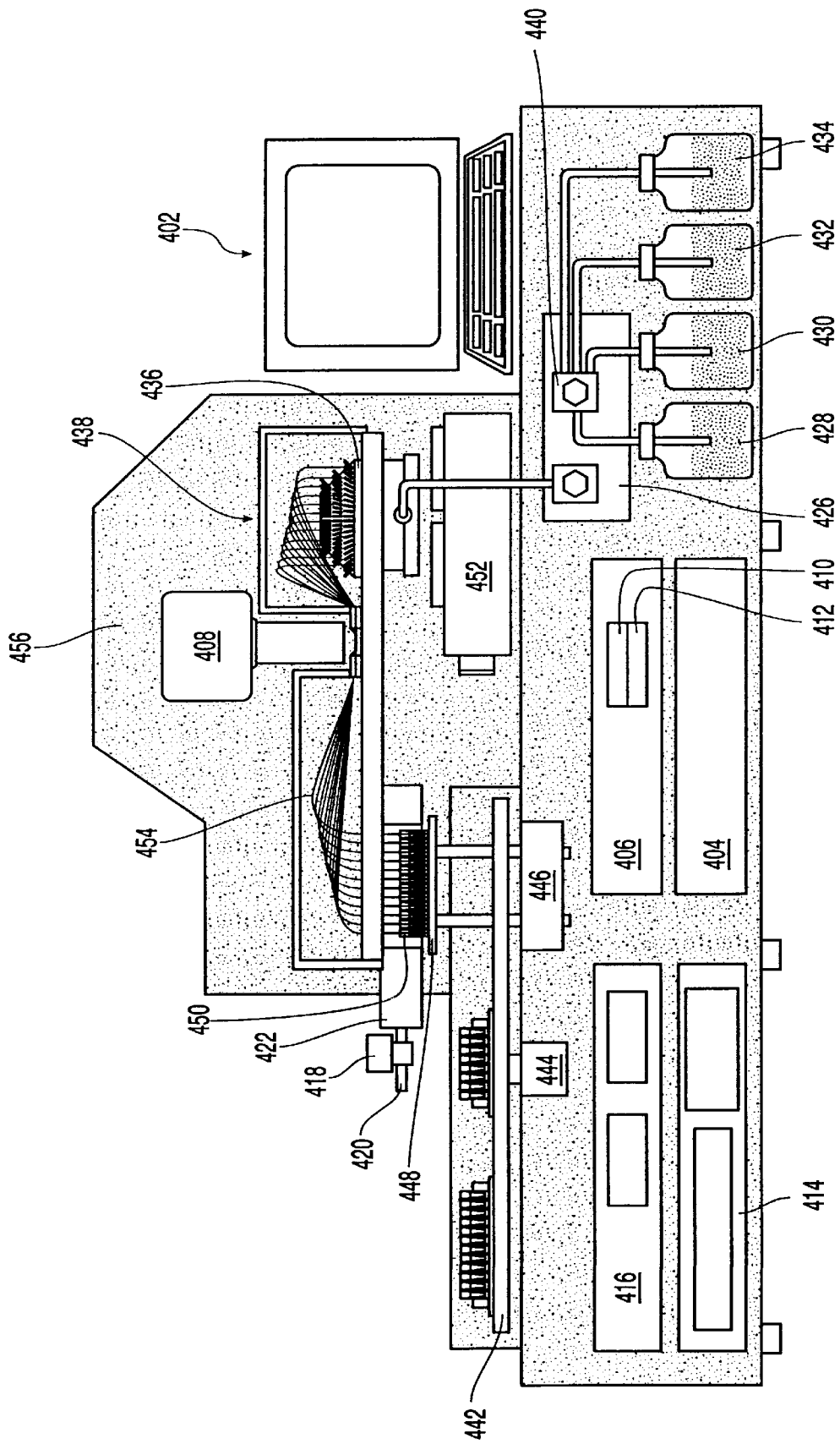
FIG. 10 shows an electrophoretic apparatus in accordance with the present invention.

FIG. 10 shows an electrophoretic apparatus 400 designed for use with a capillary cartridge formed in accordance with FIGS. 6–9. The apparatus comprises a user interface 402, shown as a video display terminal and keyboard, which communicates with a controller 404, which preferably is a microprocessor-based computer, or the like. The user interface 402 allows a user to enter commands, receive status information, and view the collected data.

The apparatus 400 also comprises a data processing computer 406, which receives, stores and processes video signals from a CCD camera 408. The data processing computer 406 is provided with optical 410 and/or magnetic 412 read/write data storage means. Resident in the data processing computer 406 are signal and image processing software to analyze the signal data from the camera 400. The data processing computer 406 is connected to the controller 404, and responds to requests from the latter, exchanging data and control information, as needed.

The apparatus 400 is further provided with a high-voltage power supply 414 which provides the necessary voltage to be applied across the ends of the capillary tubes. The power supply's operation is directed by the controller 404.

The controller 404 also directs the operation of a pump interface 416, which comprises a number of electronic switches. The pump interface 416 regulates the operation of a solenoid valve 418. The solenoid valve 418 connects a gas inlet 420 which is connected to an inert gas source, such as a pressurized helium tank, to the chamber 422. The pump interface 416 also regulates the operation of high pressure liquid chromatography (HPLC) pump 426. The HPLC pump 426, under the direction of the controller, selectively supplies liquids in containers 428, 430, 432, 434, gel, buffer solution, an acid, and a base, to a pressure cell 436 of a cartridge 438 through a multi-valve manifold 440.

A carousel 442 having a plurality of platforms 448 is turned by a rotor 444. A lifting means 446, such as a hydraulic pump or the like, raises and lowers a platform 448 positioned under a first mounting plate. This brings a microtitre tray 450 on the platform 448 towards and away from an array of capillary ends, as previously described. Both the rotor 444 and the lifting means are connected to, and driven by, the controller 404.

The apparatus 400 also includes a light source 452, preferably a laser, which illuminates the capillary tubes 454, as directed by the controller 404. The light source 452 illuminates the capillary tubes 454 from below, through an opening in a base member of the cartridge 438, as previously described. A light shroud 456 covers the camera 408, the light source 452, and at least the window region of the capillary tubes 454, as the detection of the capillary bands is performed in the dark.

During operation, the capillary tubes 454 are first cleaned and then loaded with gel through the pressure cell 436 by activating pump 452. The pump 452 is then turned off. Next, a platform 448 carrying a microtitre tray 450 holding samples is raised by the lifting means 446. This forms a seal between the platform 448 and the underside of the chamber 422. It also dips the first capillary ends into the wells of the microtitre tray 450. With the chamber 422 sealed, the solenoid valve 418 is opened, allowing pressurized helium gas to enter through the inlet 420. This puts a uniform positive pressure on the samples in each of wells of the microtitre tray 450, on the order of 30 psi, and forces the samples at least slightly into the first capillary ends. As discussed above, a high voltage may be applied for a brief period of time for this purpose, as well. The platform 448 is lowered and the carousel 442 is rotated, bringing a microtitre tray filled with buffer solution under the first capillary ends. Next, the buffer tray is raised so that the first capillary ends are dipped into the buffer solution, and the pressure cell 436 is filled with buffer solution so that the second capillary ends are in contact with buffer solution, as well. After this, the high voltage source 414 is turned on to perform the electrophoresis run. The light source 452 and the camera 408 are used to simultaneously detect the bands in all the capillary tubes 454. The video signal data from the camera 408 are processed and stored in the computer 406. The processed data may then be presented on the user interface 402. After the run, the cartridge 438 may be reconditioned (i.e., cleaned) and prepared for another run.

For optimum DNA separation and data resolution, it is best that the environmental conditions of each capillary tube be essentially the same as that of its neighbors. This helps maintain uniform conditions for the migration of DNA samples along the length of all capillaries. In this context, the environmental conditions to be controlled may include temperature, electrical interference, and magnetic interference.

As stated above, each capillary tube is preferably filled with a gel, and a voltage differential is applied to the two ends of each capillary tube. The gel has a linear electrical resistance on the order of 16 KΩ/cm. Thus, along the 65 cm length of a capillary tube, the gel has a total resistance of approximately 1 MΩ. Given an applied voltage differential between capillary ends on the order of 20 kV, a current of approximately 20 mA passes through the gel. In accordance with well-established electromagnetic principles, this current creates a magnetic field concentric about the length of a capillary tube. The intensity of the magnetic field at any given point is proportional to the current and inversely proportional to the square of the distance away from the capillary tube. The magnetic field created by any given capillary affects the electrical properties of the gel, and thus the migration of the DNA, in the neighboring capillary tubes.

Since the gel occupies the entire length of the capillary tube, there is a linear voltage gradient, on the order of 300 V/cm, along the length of the capillary tube. This effectively creates a continuous electric field along the capillary tube. In addition, as an electric field is created between any pair of separated charges, electric fields also exist between neighboring capillary tubes by virtue of the presence of the charged gel.

The interaction of electric and magnetic fields among the various gel-filled capillary tubes causes electrical crosstalk. As the crosstalk does not affect each of the tubes in the same exact manner, DNA in different tubes will migrate at slightly different rates. In a capillary cartridge, this means that DNA molecules having similar charge and weight may arrive at the window region at different times in different capillary tubes.

Figure 11A:
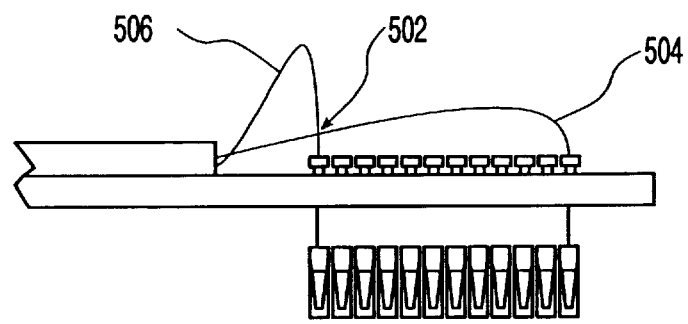
FIGS. 11a–c illustrate the capillary crossover and approaches to mitigate crosstalk.

FIG. 11a, which focuses just two of the many capillary tubes in a capillary cartridge, illustrates yet another phenomenon which exacerbates the crosstalk problem. As shown in FIG. 11a, the crossover 502 of a first capillary tube 504 and a second capillary tube 506 takes place at different points along their respective lengths. The crossover takes place quite distant from the sample end (the capillary end dipped into the DNA sample) of the first capillary tube 504, but very close to the sample end of the second capillary tube 502. Thus, the voltage potential of the gel at the crossover 502 differs for the two tubes 504, 506, ultimately resulting in an asymmetric effect on DNA migration in the two tubes. It goes without saying, then, that the asymmetries become far more complex when several dozen capillaries are involved. As a practical matter, however, these asymmetries exist only when three or more capillary tubes are arranged to work simultaneously.

As stated above, capillary tubes used in DNA sequencing are formed from fused silica having an outer diameter of about 150 microns. Commercially available capillary tubes are normally provided with a thin polyimide layer, on the order of 15 microns, formed on top of the fused silica, all along the tubes' length, for a total capillary diameter of about 180 microns. The polyimide layer is removed along a small portion of the capillary tube which enables one to have visual access to, and thereby detect, the migrating DNA samples. The polyimide layer should be thick enough to help strengthen a capillary tube, yet still thin enough to allow for heat transfer between gel, or other material, within the capillary tube and the surrounding environment. Although the polyimide layer has electrically insulative properties, and has a dielectric constant greater than that of air, its thickness is insufficient to prevent crosstalk.

Figure 11B:
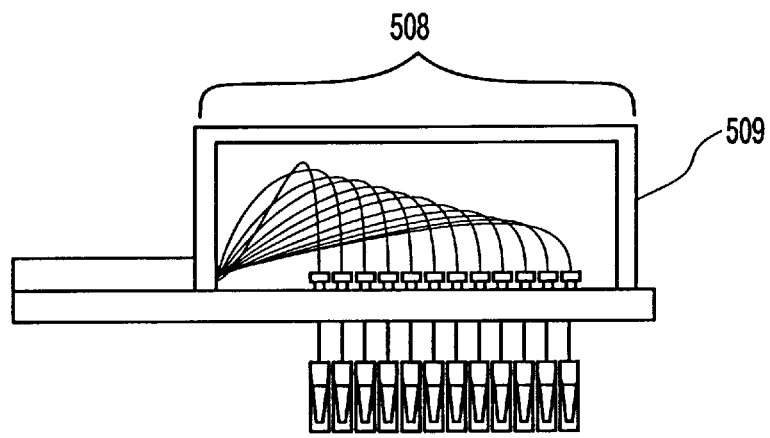

As shown in FIG. 11b, one approach to mitigating the effects of crosstalk is to surround a first portion 508 of all capillary tubes with a ⅜–½" thick polycarbonate enclosure 509. The enclosure is filled any one of a variety of highly resistive gases, fluids, gels, and other such materials. Unlike the sample in the wells into which the first capillary end is dipped for the uptake of a DNA sample, these fluids or gels are non-conductive. Preferably, these materials also have a dielectric constant greater than that of air and are good conductors of heat. As shown in FIG. 11b, the first portion 508 of the capillary tubes comprises an equal length of each of the capillary tubes, as the leftmost tubes are more bowed than those to their right. Thus, the enclosure encloses a substantially identical section of each of said capillary tubes. In the preferred embodiment, a paraffin-based liquid coolant, PARATHERM NF™, available from the Paratherm Corp. of Conshohocken, Pa., is used. Preferably, the coolant is circulated through the enclosure by means of an external pump to maintain a user-specified temperature suitable for DNA migration, in view of the gels, solvents, and other media used. The high dielectric constant of the coolant helps mitigate the effects of any electric fields between the capillary tubes.

Figure 11C:
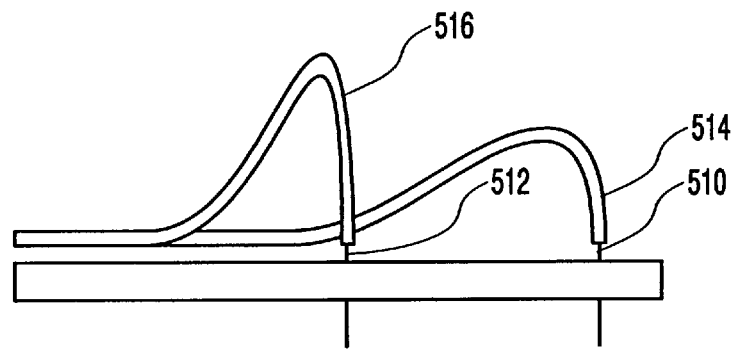

As shown in FIG. 11c, an alternative to providing an enclosure around their first portion 508 is to provide each capillary tube 510, 512 with a separate protective tube or sheathing 514, 516, respectively. The sheathing 514, 516 is formed from an electrically insulative material which surrounds the capillary tube, the capillary tubes occupying a lumen formed in each of the protective tubes 514, 516. This sheathing, which preferably has a higher dielectric constant (approximately 3.0) than that of air, would extend from very close to the sample end to a point equidistant along the lengths of all the capillary tubes. The sheathing can be made of a wide variety of materials, but thermoplastics, including olefins such as polyethylene, or fluorocarbons, such as polytetrafluorethylene are advantageous. In general, fluorocarbons are preferred for mitigating crosstalk while other thermoplastics are easier to work with since they are more amenable to bonding with adhesives. Single-lumen tubing formed from PEEK, polypropylene and Teflon, available from Small Parts, of Miami Lakes, Fla., can be used for this purpose.

Using either an enclosure, as shown in FIG. 11b, or individual sheathing, as shown in FIG. 11c, protects that portion of the capillary tubes closest to a first end of the capillary tubes, which are dipped into the DNA sample. After this portion 508, the capillary tubes are arranged in parallel, side-by-side relation, until they pass the window region, in which DNA migration within the capillary tubes may be viewed. With the capillary tubes laying side-by-side, asymmetric crosstalk still occurs because each capillary tube has a different number of neighbors on either side. As shown in FIGS. 12a and 12b, given twelve capillary tubes laying side-by-side, the two shaded capillary tubes 510' in each figure have equal numbers of neighbors on both sides. In theory, then, the crosstalk effects due to their neighbors should be similar for these two. However, the crosstalk effect is dissimilar for any other "unbalanced" pair, as there is no symmetry in the number of neighbors on both sides. Thus, the two shaded capillary tubes 510" in FIG. 12c are affected by crosstalk differently.

Between this first portion in which the capillary tubes are bowed, and the window region, the capillary tubes will typically extend parallel to one another. In this regard, the capillaries may run side-by-side in a ribbon-like assembly, or together as the bundle in a cable-like assembly, or even in multiple rows, either stacked on atop of one another, or interleaved. The electric and magnetic crosstalk is particularly significant when they are so arranged, mainly due to the close proximity of the capillary tubes to one another.

Figure 13A:
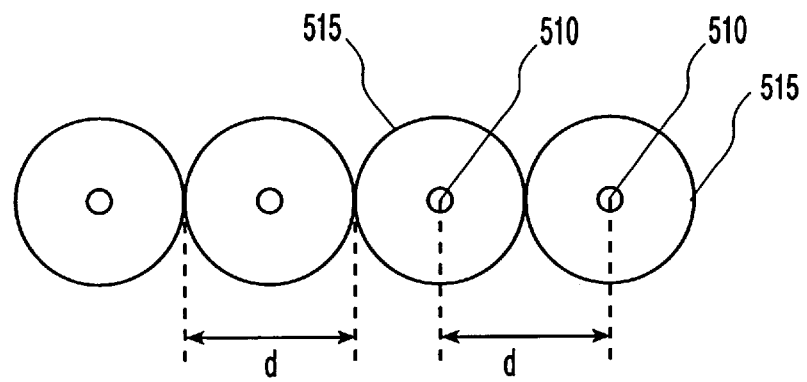
FIGS. 13a–c show approaches for mitigating crosstalk.

One solution to this problem is to provide each capillary tube with a thick, individual sheathing between the first portion and a point proximate to the window. This thick sheathing would attenuate crosstalk not only by virtue of its high dielectric constant, which is greater than that of air, but also because it physically spaces apart the capillary tubes. As shown in FIG. 13a, the distance d between the centers of neighboring capillary tubes 510 results from the thick sheathing 515. Such thick sheathing can, by itself, significantly contribute to mitigating crosstalk. For instance, if the thick sheathing 515 has an outer diameter d of 1/16", then adjacent capillary tubes 510 would have their centers 1/16" apart. This contrasts with the 150–180 micron (approx. 0.006–0.007") spacing between the centers of two unsheathed, abutting capillary tubes. Thus, the sheathing separates the capillary tubes by a distance equal to at least a diameter of a capillary tube. Preferably, however, the separation between neighboring capillary tubes is on the order of 5–10 diameters of a single capillary tube. However, one drawback of sheathing spacing apart capillary tubes by ten diameters is that a micro-titre tray-worth of ninety-six thickly sheathed capillary tubes, laid side-by-side, would form a 6" wide ribbon.

The thick sheathing surrounding each capillary tube can be provided with an oversized lumen in which the capillary tube is positioned. A gaseous or liquid coolant material can be circulated through the lumen using a pump or other equivalent means. The coolant material helps maintain a uniform temperature across the cross-section of each capillary tube, all along the length of the sheathing.

The thick sheathing may also be provided with a thin conductive coating to further enhance electrical performance during electrophoresis. This coating is preferably applied to the outside of the sheathing, although it may be applied to the inner walls of the lumen instead. In the preferred embodiment, NICKEL PRINTS™, available from GC Electronics, Rockford Ill., is used to coat the thick sheathing. It is possible, however, to use other metal paints, conductive polymers and the like for this purpose.

During use, the conductive coating is maintained at a predetermined voltage level along the entire length of the sheathing by connecting it to a suitable voltage source. Preferably, this voltage level is the same as that applied at one end of the capillary tubes during electrophoresis, since one only need electrically connect the conductive coating to the same voltage source used to drive that end of the capillary tubes. Thus, it is most expedient to keep the conductive coating at zero volts (i.e., ground), or at the high voltage level used during electrophoresis. Coating the sheathing surrounding each capillary tube, and maintaining this sheathing at the same potential for all capillary tubes, help ensure that stray capacitances and other electrical factors associated with the sheathing affect all the capillary tubes in substantially the same way.

While it preferred that one apply the conductive coating to the sheathing, it may even be possible to achieve this same effect by directly coating the capillary tubes with the conductive material, between the first end of the capillary tubes and the window region. If this is done, one must ensure that dielectric breakdown of the fused silica or the polyimide coating due to a high voltage differential in a radial direction between the material inside the capillary tube and the conductive coating outside the capillary tube, does not takes place. One must also ensure that arcing between disparately charged portions of the coated capillary tube does not take place, either.

Instead of being arranged in linear fashion, as shown in FIG. 13a, the thickly sheathed capillary tubes can simply be bundled together, much as a collection of straws. Here, too, the thick sheathing helps mitigate crosstalk. Regardless of how the thickly sheathed capillary tubes are arranged, the sheathing is discontinued proximate to the window region. Then, the naked capillary tubes converge to form a narrow ribbon having a total width of about 1.5 cm, which is more amenable for detection purposes.

Figure 13B:
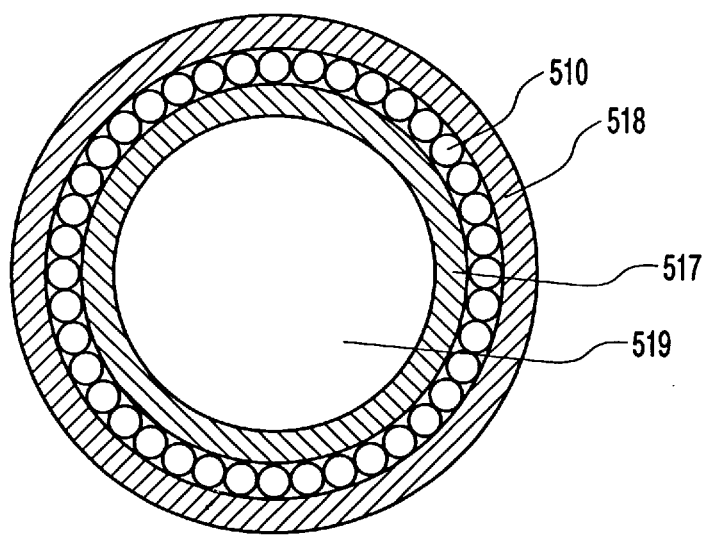
Figure 13C:
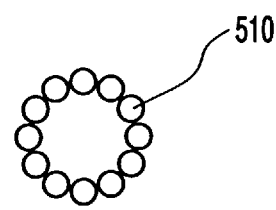

A second solution to this problem is to spatially arrange the capillary tubes so that the cumulative crosstalk effect on one is substantially the same as on all the others. As shown in FIG. 13b, this can be achieved, for instance, by adhesively joining a single layer of at least three capillary tubes 510 side-by-side, such as with an epoxy, so that they abut each other, around a cylindrically-shaped structural support member 517. In such case, each capillary tube 510 extends parallel to a longitudinal axis of the cylindrical support member 517. When only a few tubes are present, or when the support member has a larger diameter than necessary, one can space apart the capillary tubes at equal intervals around the support member. As shown in FIG. 13c, it may even be possible to simply arrange the capillary tubes in a circle and join them to each other with the epoxy or other suitable adhesive, thus altogether doing away with the support member.

When a support member is used, it can be formed from rubber, plastic, polycarbonate, wood, and even other materials. Preferably, these materials would be non-electrostatic so as not to contribute to any electrical interference when the capillary tubes are in use. The support member 517 may be provided with a central passageway 519. Air or a liquid coolant may pass through this passageway 519 to help regulate the temperature of the capillary tubes 510 affixed to the outer surface of the support member 517.

The capillary tubes may be protected from physical damage by surrounding them, whether or not they have a support member, with protective tubing 518 formed from teflon, polyethylene, or other suitable material. An epoxy adhesive is again preferred for securing the capillary tubes to the protective tubing 518.

A hybrid solution can also be used to mitigate crosstalk in a region between the first portion and the window region. This is done by arranging all capillary tubes in such a manner that all capillary tubes are affected by their neighbors in substantially the same manner. Such an arrangement is shown in FIGS. 14a–c, in which protective tubing 520 is provided with a multiplicity of through-passages, or lumens, spaced evenly about a circle formed along a periphery of the tubing. A capillary tube is situated in each of the lumens, and so all capillary tubes are arranged in the same manner relative to one another. As stated above, this configuration is advantageous in situations where there are at least three capillary tubes.

The capillary tubes 524 indicated in FIG. 14a will have a different crosstalk effect on each other, as compared to the capillary tubes 526 indicated in FIG. 14b or the capillary tubes 528 indicated in FIG. 14c. However, if each lumen is occupied by a capillary tube, the overall crosstalk effect on any one capillary tube is substantially the same.

If there are more lumens than capillary tubes, the overall crosstalk effect on any one capillary tube may again be the same so long as the capillary tubes are arranged in a symmetrical manner. For instance, if 12 lumens are provided, one may only insert a capillary tube into every second, every third, every fourth, or every sixth lumen, while still maintaining crosstalk symmetry. Thus, it may be possible for the protective tubing to have a first number of lumens formed therein, with a second number of capillaries occupying some of the lumens, the second number not being greater than the first number. Another option to maintain crosstalk symmetry when not all capillary tubes are needed is to provide "dummy" tubes into which no DNA sample is introduced. Thus, if only, say, seven of the twelve capillary tubes need to be used, all 12 capillary tubes would be filled with medium, but DNA samples would only be introduced into seven of them. The remaining capillary tubes, however, would be subject to the same voltage difference across their ends. This should that each capillary tubes will be subject to same magnetic and electric field as its neighbors.

In FIGS. 14a–c, the protective tubing having a circular cross-section is shown to have a plurality of lumens formed therein. The multi-lumen tubing of FIGS. 14a–c is provided with 12 lumens spaced evenly about a circle along the periphery of the tubing. It should be noted however, that a different number of lumens may be provided so long as they are symmetrically spaced relative to one another, so as to accommodate a predetermined number of spaced apart capillary tubes. Also, the protective tubing 520 need not have a circular cross-section. For instance, it may have a equilateral triangular cross-section, with only three lumens being provided at the corners, or a square cross-section with four lumens, each provided at one of the corners, or, alternatively, at corresponding points along each edge between each pair of corners. What is important is that the relative spacing between one capillary tube and its neighbors be such that the net effect of all pairwise crosstalks for that capillary tube is substantially the same for all capillary tubes. This means that the lumens, and therefore the capillary tubes held within them, are arranged such that the pairwise distances from any one lumen to the remaining lumens formed in the protective tubing 520, are the same for all lumens.

In addition to spacing the capillary tubes to mitigate crosstalk, further mitigation may be achieved by judicious choice of the material used to form the multi-lumen protective tubing 520. Preferably, the protective tubing 520 is formed from a thermoplastic or fluorocarbon (e.g., TEFLON™) material. Fluorocarbon is better for mitigating crosstalk, as it has a higher dielectric constant than olefins such as polyethylene. However, thermoplastics are easier to work with when it comes to bonding the multi-lumen protective tubing to other components of a capillary cartridge. In the preferred embodiment, low density polyethylene (LDPE), part no. #7791, available from Dow Chemical was used.

The outer diameter of the 12-lumen protective tubing 520 of FIGS. 14a–c must be large enough to provide a fair degree of structural rigidity so as to protect the capillary tubes from damage during transport and ordinary use. In the preferred embodiment of FIGS. 14a–c, the protective multi-lumen tubing has a ¼" outer diameter with its lumens having a diameter of 0.035".

The diameter of each lumen 522 must be large enough to accommodate the diameter of a capillary tube which is threaded therethrough. The 0.035" lumen diameter is larger than absolutely necessary to accommodate a capillary tube, with its outer diameter of approximately 150–180 microns. This provides an annular space between the capillary tube and the wall of the lumen. On average, the width of the annular space is about 0.014". The annular space serves two purposes. First, it allows some freeplay for the capillary tubes held in the lumens. Thus, one can bend the protective tubing 520 without fear of damaging the capillary tubes, as the capillary tubes may slide, very slightly, relative to the lumen wall. Second, and more importantly, the space allows air or liquid coolant to pass through the lumen and bathe the capillary tubes, thus providing a measure of temperature regulation and additional mitigation of crosstalk.

Figure 15:
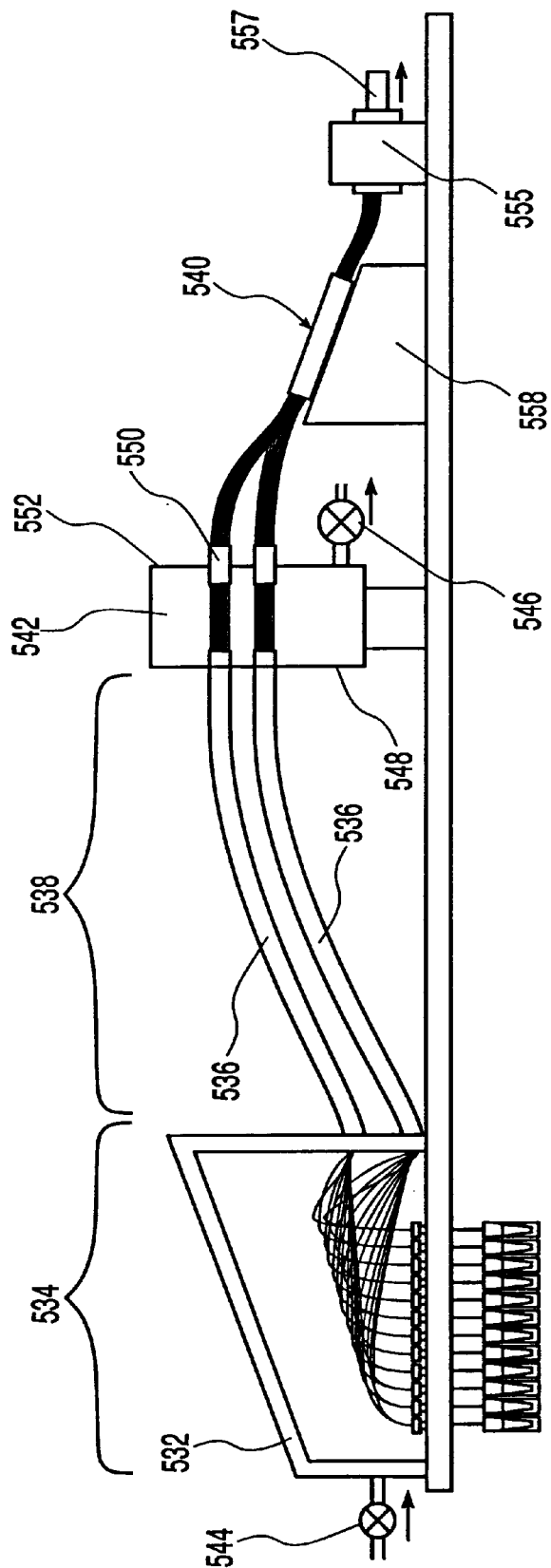
FIG. 15 shows a capillary cartridge employing multi- and single-lumen tubing to mitigate crosstalk.

FIG. 15 depicts a capillary cartridge 530 configured to circulate a liquid coolant both in an enclosure 532 near the first portion 534 the capillary tubes, and also through multi-lumen protective tubing 536 along a second portion 538 of the capillary tubes between the first portion 534 and the window region 540. The multi-lumen protective tubing 536 is directly attached to the enclosure 532 and is sealed thereto by means, for example, of an epoxy or other adhesive. Thus, the coolant in the enclosure 532 is in communication with the coolant in the lumens of the protective tubing 536.

The multi-lumen protective tubing 536 passes through a first wall 548 of a coolant collection box 542 within which it terminates. The coolant collection box 542 is situated shortly before the window region 540. An epoxy, or other, adhesive is used to secure the multi-lumen protective tubing 536 to the first wall 548 of the coolant collection box 542. This helps ensure that coolant does not leak between the enclosure 532 and the coolant collection box 542.

The coolant collection box 542 serves two purposes. The first purpose is to provide a terminus for the coolant within the capillary cartridge. When it is circulated, the coolant enters the enclosure 532 through valve 544, passes through the lumens in the multi-lumen protective tubing 536 where it bathes the capillary tubes, enters the coolant collection box 542, and then exits the latter via valve 546, from whence it goes to a circulating pump. The arrow pointing in the direction of valve 544 and the arrow pointing away from valve 546 depict the general direction of fluid flow. Valves 544 and 546 may be closed when circulation is not desired. With the valves closed, the coolant will still bathe the capillary tubes, but it will not precisely control their temperature within a predetermined range.

The second purpose of coolant collection box 542 is to provide an interface region which allows the bundled capillaries in the multi-lumen protective tubing 536 to become unbundled without the leakage of coolant. As shown in FIG. 15, the capillary tubes exit the multi-lumen protective tubing 536 while in the coolant collection box 542. Upon exiting the multi-lumen protective tubing, the capillary tubes are still bathed in the coolant. The capillary tubes in each bundle then enter a single-lumen tubing 550 which passes through a second wall 552 of the coolant collection box 542. The single-lumen tubing 550 is secured to the wall by means of an epoxy adhesive. This prevents coolant from leaking out of the coolant collection box 542 via the openings in second wall 552, which openings are formed to accommodate the single-lumen tubing 550. In the most preferred embodiment, the single-lumen tubing has a ¼" outer diameter and a single ⅛" diameter lumen.

The capillary tubes within the single-lumen tubing 550 are encased in a UV-cured epoxy, or similar, adhesive material 554. The UV-cured adhesive protects the capillary tubes from damage as then emerge from the coolant collection box 542. It also acts as a barrier, preventing the leakage of coolant through the single-lumen tubing 550. As such, the UV-cured lumen is exposed to the coolant inside the coolant collection box 542, and is also exposed to the air outside the box.

Figure 16A:
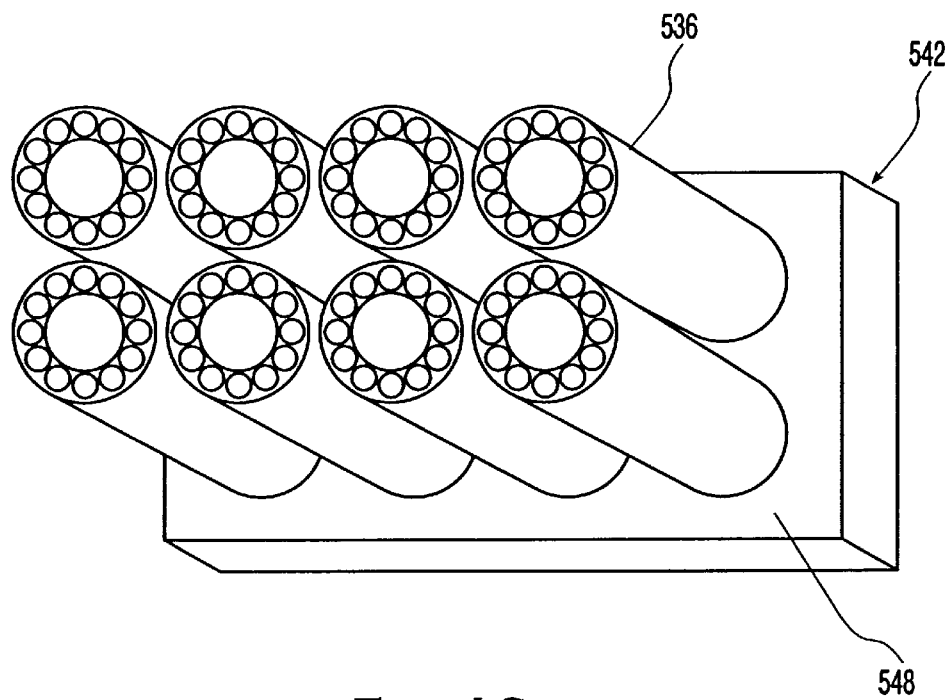
FIGS. 16a–b show a detailed view of the arrangement of the tubing.

As shown in FIG. 16a, the capillary tubes, as they enter the coolant collection box 542, are arranged as a spaced apart bundle having a spatial arrangement dictated by the location of the lumens. In the preferred embodiment of 96 capillary tubes, each multi-lumen tube has 12 capillary tubes. Eight of these multi-lumen tubes, arranged in two horizontal rows of four multi-lumen tubes each, enter the coolant collection box 542. This two-by four arrangement is selected, as it easily fits into the first wall 548 of the box 542. Alternate configurations of the eight multi-lumen tubes may also suffice.

Figure 16B:
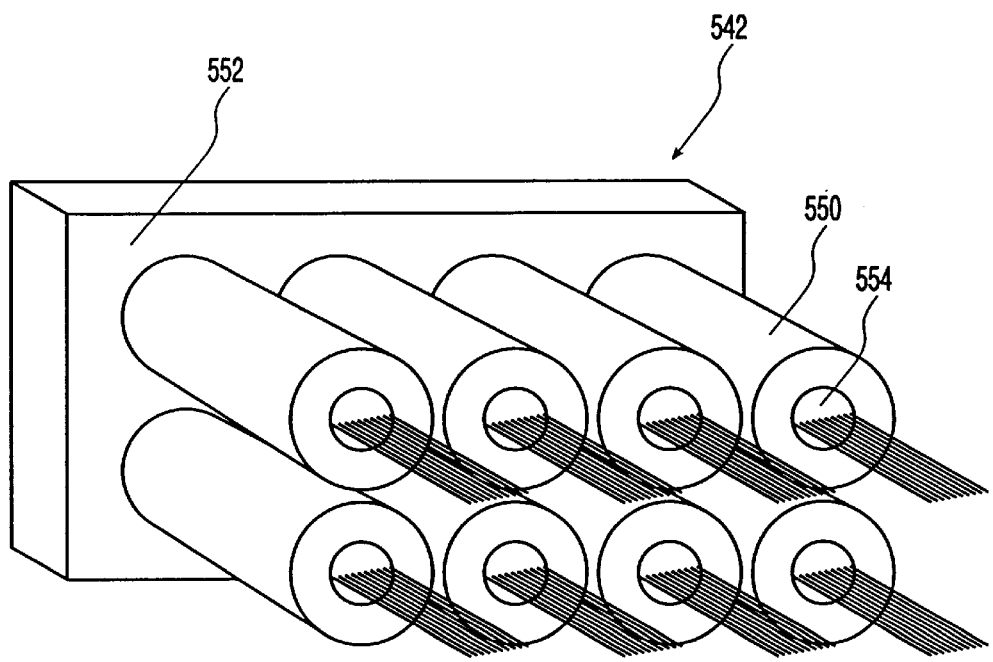

As shown in FIG. 16b, eight single-lumen tubes, also arranged in two horizontal rows of four tubes each, emerge from the second wall 552 of the coolant collection box 542. The capillary tubes secured in each of the single-lumen tubes are arranged side-by-side in a linear array as they emerge from the single-lumen tubing 550.

Upon emerging from the single-lumen tubing 550, the various linear arrays are brought together side-by-side to form a single capillary ribbon. As stated above, in the preferred embodiment, there are eight multi-lumen tubes, each having 12 lumens, thus accommodating a total of ninety-six capillary tubes. The ninety-six capillary tube-wide ribbon has a total width on the order of only 1.44–1.73 cm, as each capillary tube is only about 150–180 microns wide.

By the time the capillary tubes emerge from the single-lumen tubing 550, most of the DNA migration and separation will already have taken place. Nevertheless, as the capillary tubes emerge into air, crosstalk can still occur. Therefore, it is best to minimize the exposure to air in this third region, which extends from the point at which the capillary tubes emerge from the single-lumen tubing 550 to the window region 540. In this third region, it is usually impractical to provide each of capillary tubes with individual sheathing due to the web-like nature of the interleaved capillaries as they assume a linear array. Therefore, the coolant collection box 542 should be positioned as close to the window region as possible, without compromising the integrity of the capillary tubes as they approach the window region.

From the foregoing, it should be apparent that the capillary tubes are surrounded by fluid from a first end thereof, to nearly the window region. Of course, this fluid cannot extend all the way to the openings formed in the first ends, as the openings must be free so that they may be dipped into the samples. Therefore, the non-conductive fluid, though surrounding the capillary tubes along a substantial portion thereof, never enters the tubes themselves.

As seen in FIG. 15, the capillary tubes, when in the window region 540, are supported by a window pedestal 558, which rests atop the base member 556 of the capillary cartridge. As shown in FIG. 15, the ribbon of capillary tubes is slightly sloped towards the base member 556. It should be noted that this sloped configuration is not absolutely essential, as it is feasible to arrange the capillary ribbon in virtually any orientation, subject to the positions of the illumination means and the detection means. Regardless of the orientation of the capillary ribbon, the capillary tubes pass from the window region and enter a high pressure fitting 555 near the second capillary ends. High pressure fitting 555 is provided with an outlet 557 which, in turn, provides access to sources for gel, buffer, solvents, and other materials.

While the above invention has been described with reference to certain preferred embodiments, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. An electrophoretic apparatus comprising:
    at least three capillary tubes, each capillary tube having first and second capillary ends, and a window region formed therebetween, and
    an electrically insulative material having a dielectric constant greater than that of air surrounding each capillary tube along at least a predetermined length thereof, said predetermined length being situated between said first capillary end and said window region,
    wherein said electrically insulative material comprises at least one protective tube having at least one lumen formed therein, and said capillary tubes are situated in said at least one lumen along said first portion,
    said capillary tubes are arranged substantially parallel to one another along a first portion of said predetermined length
    said at least one protective tube is provided with a first number of lumens, each of a second number of said lumens being occupied by a single capillary tube, said second number being not greater than the first number, and
    at least one of said first and second number of lumens is arranged such that a collection of pairwise distances from any one lumen in that number to the remaining lumens in that number is substantially the same for all lumens in that number.

2. The apparatus of claim 1, comprising a plurality of protective tubes, each protective tube having said first number of lumens formed therein, said lumens being spaced evenly about a circle formed along a periphery of each of the protective tubes.

3. The apparatus of claim 2, comprising eight protective tubes, each protective tube having twelve lumens formed therein.

4. The apparatus of claim 1, further comprising a coolant material occupying each of said lumens.

5. The apparatus of claim 4, further comprising means for circulating said coolant material through said lumens.

6. The apparatus of claim 1, further comprising an enclosure enclosing a substantially identical second portion of each of said capillary tubes, wherein said second portion is closer to the first capillary end than the first portion, and said protective tube is connected, at a first end thereof, to said enclosure.

7. The apparatus of claim 6, further comprising a coolant collection box connected to a second end of said protective tube at a point before said window region, wherein said capillary tubes emerge from a wall of said coolant collection box, and a coolant material occupies said enclosure, said lumens, and said coolant collection box.

8. The apparatus of claim 7, further comprising a high pressure fitting connected to said second capillary ends.

9. The apparatus of claim 1, further comprising a coating of conductive material on at least one of an inner wall of said lumen and an outer wall of said protective tube.

10. An electrophoretic apparatus comprising:

at least three capillary tubes, each capillary tube having first and second capillary ends, and a window region formed therebetween, and an electrically insulative material having a dielectric constant greater than that of air surrounding each capillary tube along at least a predetermined length thereof, said predetermined length being situated between said first capillary end and said window region, wherein said capillary tubes are arranged substantially parallel to one another along a first portion of said predetermined length, said electrically insulative material comprises at least one protective tube having at least one lumen formed therein, said capillary tubes are situated in said at least one lumen along said first portion, and said capillary tubes are arranged relative to one another such that a collection of pairwise distances from any one capillary tube to the remaining capillary tubes is substantially the same for all capillary tubes, along said first portion.

11. The apparatus of claim 10, further comprising a structural support member positioned within said lumen and extending substantially along said first portion, with said capillary tubes being fixed to said structural support member.

12. The apparatus of claim 11, further comprising a passageway formed within said structural support member, said passageway extending substantially along said first portion, a coolant material occupying said passageway.

13. The apparatus of claim 12, further comprising means for circulating said coolant material through said passageway.

14. An apparatus comprising:

at least three capillary tubes, each capillary tube having first and second capillary ends, and a window region formed therebetween, said capillary tubes being arranged substantially parallel to one another along a first portion between said first capillary end and said window region, wherein said capillary tubes are arranged relative to one another such that a collection of pairwise distances from any one capillary tube to the remaining capillary tubes is substantially the same for all capillary tubes, along said first portion.

15. An apparatus comprising:

a first mounting plate having a first side and a second side and having an array of plate holes formed therein; and at least three capillary tubes, each having first and second capillary ends, each capillary tube being retained in one of said plate holes proximate to its first capillary end, said first capillary end projecting on said first mounting plate first side, wherein centers of said projecting first capillary ends are spaced apart from one another, forming an array of first capillary ends, said array of first capillary ends having a spatial arrangement corresponding to that of an array of wells associated with a microtitre tray of standard size, and said capillary tubes are arranged parallel to one another at a window region thereof, a length from said first capillary ends to said window region being substantially the same for all capillary tubes, wherein said capillary tubes are arranged relative to one another such that a collection of pairwise distances from any one capillary tube to the remaining capillary tubes is substantially the same for all capillary tubes, along a first portion thereof.

16. An electrophoretic apparatus comprising:

at least three capillary tubes, each capillary tube having first and second capillary ends, and a region formed therebetween; and at least one protective tube surrounding the capillary tubes along said region;

wherein said at least one protective tube is provided with a first number of lumens, each of a second number of said lumens being occupied by a single capillary tube, said second number being not greater than the first number, and at least one of said first and second number of lumens is arranged such that a collection of pairwise distances from any one lumen in that number to the remaining lumens in that number is substantially the same for all lumens in that number.

* * * * *